US006993377B2

(12) United States Patent
Flick et al.

(10) Patent No.: US 6,993,377 B2
(45) Date of Patent: Jan. 31, 2006

(54) METHOD FOR DIAGNOSING HEART DISEASE, PREDICTING SUDDEN DEATH, AND ANALYZING TREATMENT RESPONSE USING MULTIFRACTAL ANALYSIS

(75) Inventors: James T. Flick, Little Rock, AR (US); Jacob Joseph, Little Rock, AR (US)

(73) Assignee: The Board of Trustees of the University of Arkansas, Little Rock, AR (US)

(*) Notice: Subject to any disclaimer, the term of this patent is extended or adjusted under 35 U.S.C. 154(b) by 676 days.

(21) Appl. No.: 10/080,421

(22) Filed: Feb. 22, 2002

(65) Prior Publication Data

US 2003/0163057 A1 Aug. 28, 2003

(51) Int. Cl.
A61B 5/0452 (2006.01)

(52) U.S. Cl. .................................................... 600/509
(58) Field of Classification Search .......... 600/508–521
See application file for complete search history.

(56) References Cited

U.S. PATENT DOCUMENTS 5,471,991 A * 12/1995 Shinnar

OTHER PUBLICATIONS

"Predicting Survival in Heart Failure Case and Control Subjects by Use of Fully Automated Methods for Deriving Nonlinear and Conventional Indices of Heart Rate Dynamics;" Kalon K.L. Ho, MD, et al; *American Heart Associaton, Inc.*, 1997; 96:842–848.
Abstract from PubMed: "Dynamic Analysis of Heart Rate May Predict Subsequent Ventricular Tachycardia after Myocardial Infarction;" Makikallio TH, et al; *American Journal of Cardiology*, Sep. 15, 1997; 80(6): 779–83.
Abstract from PubMed: "Heart Rate Dynamics in Patients with Stable Angina Pectoris and utility of Fractal and Complexity Measures;" Makikallio TH, et al; *American Journal of Cardiology*, Jan. 1, 1998; 81 (1):27–31.

(Continued)

*Primary Examiner*—Scott M. Getzow
(74) *Attorney, Agent, or Firm*—J. Charles Dougherty

(57) ABSTRACT

A method of analyzing electrocardiogram (EKG) data for use in the diagnosis of heart disease, prognosis of cardiac conditions, and the monitoring of heart disease therapies is disclosed. The method utilizes a wavelet-based multifractal analysis with one or more of (1) a discrete wavelet smoothing step to remove the effects of abnormal beats; (2) "Levy flight" analysis to detect the frequency of abnormal beats known to adversely affect the multifractal (MF) analysis; and (3) MF alpha analysis, a multifractal extension of monofractal short term (ST) alpha analysis. The invention further comprises an EKG test battery comprising Levy flight anomalous beat/beat cluster screening, followed by (ST) MF alpha analysis and MF Holder analysis (when validated by the Levy flight analysis). The wavelet smoothing step can also be used to classify human EKGs by observing the effect of sequential smoothing on the MF Holder coefficient. Alternative choices to the wavelet smoothing approach to removal of abnormal beat effects include probability distribution function analysis to determine the MF Holder coefficient directly, abnormal beat ridge skeleton removal to remove the offending beats based on a direct multifractal spectrum calculation, and the calculation of various types of entropy coefficients for the EKG time series.

96 Claims, 34 Drawing Sheets

(33 of 34 Drawing Sheet(s) Filed in Color)

OTHER PUBLICATIONS

"Fractal Correlation Properties of R–R Interval Dynamics and Mortality in Patients with Depressed Left Ventricular Function after an Acute Myocardial Infarction;" Heikki V. Huikuri, MD, et al; *Circulation*, 2000;101:47–53.

Abstract from PubMed: "Fractal Analysis of Heart Rate Dynamics as a Predictor of Mortality in Patients with Depressed Left Ventricular Function after Acute Myocardial Infarction. TRACE Investigators. TRAndolapril Cardiac Evaluation;" Makkikallio TH, et al; *American Journal of Cardiology*, Mar. 15, 1999; 83(6):836–9.

Abstract from PubMed: "Fractal Analysis and Time–and Frequency–Domain Measures of Heart Rate Variability as Predictors of Mortality in Patients with Heart Failure;" Makikallio TH, et al; *American Journal of Cardiology*, Jan. 15, 2001; 87(2): 178–82.

"Scale Specific and Scale Independent Measures of Heart Rate Variability as Risk Indicators;" Y. Ashkenazy, et al; *Los Alamos arXiv:physics/9909029*, Sep. 17, 1999.

Abstract from PubMed: "Reversal of Deteriorated Fractal Behavior of Heart Rate Variability by Beta–Blocker Therapy in Patients with Advanced Congestive Heart Failure;" Lin LY, et al; *Journal of Cardiovascular Electrophysiol*, Jan. 2001; 12(1):26–32.

"Altered Complexity and Correlation Properties of R–R Interval Dynamics Before the Spontaneous Onset of Paroxysmal Atrial Fibrillation;" Saila Vikman, MD, et al.; *Circulation* Nov. 16, 1999; 2079–84.

"Multifractality in Human Heartbeat Dynamics;" Plamen Ch. Ivanov, et al; *Nature*, vol. 399, Jun. 3, 1999, 461–65.

"Behavioral–Independent Features of Complex Heartbeat Dynamics;" Luis A. Nunes Amaral, et al; *Los Alamos arXiv:cond–mat/0106508*, vol. 1, Jun. 25, 2001.

Behavioral–Independent Features of Complex Heartbeat Dynamics; Luis A. Nunes Amaral, et al; *Physical Review Letters*; vol. 86, No. 26; Jun. 25, 2001; 6026–29.

"The Multifractal Formalism Revisted with Wavelets;" J.F. Muzy, et al.; *International Journal of Bifurcation and Chaos*, vol. 4, No. 2 (1994) 245–302.

"A Multifractal Wavelet Model with Application to Network Traffic," Rudolf H. Riedi, et al; *IEEE Transactions on Information Theory*, Apr. 1999.

"Singularity Detection and Processing with Wavelets;" Stephane Mallat, et al; *IEEE Transactions on Information Theory*, vol. 38, No. 2, Mar. 1992, 617–43.

"Characterization of Self–Similar Multifractals with Wavelet Maxima;" Wen–Liang Hwang, et al; *Technical Report* 641, Jul. 1993.

"A Wavelet–Based Method for Multifractal Image Analysis;" A. Arneodo, et al; *European Physical Journal B*, 15, 567–600 (2000), 567

"Dynamic Behavior and Autonomic Regulation of Ectopic Atrial Pacemakers;" Heikki V. Huikuri, MD, et al; *Circulation*, Sep. 28, 1999, 1416–1422.

"Effects of Exercise and Passive Head–up Tilt on Fractal and Complexity Properties of Heart Rate Dynamics;" Mikko P. Tulppo, et al; *American Journal Physiol Heart Circ Physiol* 280: H1081–H1087, 2001.

Abstract: "Chaotic Advection in a Two–Dimensional Flow: Levy Flights and Anomalous Diffusion;" T.H. Solomon, et al; *Physica D* 76 70–84 (1994).

Abstract: "Long–Range Anticorrelations and Non–Gaussian Behavior of the Heartbeat;" C.–I. Peng, J.; *Physical Review Letters*, vol. 70, No. 9, 1343–46 (Mar. 1, 1993).

Abstract: "Wavelet Methods for Time Series Analysis;" Donald B. Percival, et al; *Cambridge Series in Statistical and Probabilistic Mathematics*, Oct. 5, 2000.

"A Wavelet–Based Method for Multifractal Image Analysis;" N. Decoster, et al; *The European Physical Journal B* 15, 739–764 (2000).

"A Wavelet–Based Method for Multifractal Analysis;" S.G. Roux, et al; *The European Physical Journal B 15*, 765–786 (2000).

"Direct Multifractal Spectrum Calculation from the Wavelet Transform;" Z.R. Struzik; *Information Systems (INS)*; R9914; Oct. 31, 1999; 1–10.

"Dimension and Product Structure of Hyperbolic Measures;" Luis Barreira, et al.; *Ann. of Math.* (2) 149 (1999), 755–783.

"Variational Principles and Mixed Multifractal Spectra;" L. Barreira; *Trans. Amer. Math. Soc.* 353 (2001), 3919–3944.

"The Rate of Entropy Increase at the Edge of Chaos;" Vito Latora; *Physics Letters A* 273 (2000) 97–103.

"On a General Concept of Multifractality: Multifractal Spectra for Dimensions, Entropies, and Lyapunov Exponents, Multifractal Rigidity;" Luis Barreira, et al; *Chaos* 7 (1997), No. 1, 27–38.

Abstract: "Dimension Theory in Dynamical Systems;" Pesin, Yakov B.; *Contemporary Views and Applications, xii*, 305 p. 1997 Series (CLM).

"Characteristic Distributions of Finite–Time Lyapunov Exponents;" Awadhesh Prasad, et al; *Physical Review E*, vol. 60, No. 3, Sep. 199, 2761–2766.

Generalization of the Kolmogorov–Sinai Entropy: Logistic– and Periodic–Like Dissipative Maps at the Chaos Threshold;: Ugur Tirnakli et al; *Los Alamos arXiv.cond–mat/ 0005210*, vol. 1, May 12, 2000, 1–12.

"Application of the Wavelet Transform in the laminar Turbulent Transition for a Flow in a Mixed Convection Phenomenon;" C. Abid, et al; *The European Physical Journal B* 13, 707–714 (2000).

"A Multifractal Random Walk;" E. Bacry et al; *Los Alamos arXiv:cond–mat/0005405*; May 24, 2000.

"Singularity Spectra of Rough Growing Surfaces from Wavelet Analysis;" M. Ahr, et al; *arXiv:cond–mat/9912437*, vol. 2; Apr. 3, 2000.

Modeling Heart Rate Variability by Stochastic Feedback;: Luis A. Nunes Amaral; *Computer Physics Communications*, 121–122 (1999) 126–128.

"Scale–Independent Measures and Pathologic Cardiac Dynamics;" Luis A. Nunes Amaral, et al; *Physical Review Letters*, vol. 81, No. 11, Sep. 14, 1998, 2388–2391.

"Fractal Analysis for Social Systems;" C.M. Arizmendi: *Los Alamos arXiv:adap–org/9910001*; Oct. 14, 1999.

"Oscillating Singularities on Cantor Sets; A grand–canonical multifractal formalism;" A. Arnedo; May 22, 1996.

Abstract: "Thermodynamics of Fractal Signals Based on Wavelet Analysis; application to fully developed turbulence data and DNA sequences;" A. Arneodo; *Physica A: Statistical Mechanics and Its Applications*; vol. 254 (1–2) (1998) 24–45.

"Singularity Spectrum of Multifractal Functions Involving Oscillating Singularities;" A. Arneodo.

"Intermittency, Log–Normal Statistics, and multifractal Cascade Process in High–Resolution Satellite Images of Cloud Structure;" A. Arneodo; *Physical Review Letters*, vol. 83, No. 6, Aug. 9, 1999, 1255–1258.

"Wavelet Based Multifractal Analysis of Rough Surfaces: Application to Cloud Models and Satellite Data;" J. Arrault, et al; *Physical Review Letters*; vol. 79, No. 1, Jul. 7, 1997, 75–78.

"Magnitude and Sign Correlations in Heartbeat Fluctuations;" Yosef Ashkenazy, et al; *Los Alamos arXiv:cond-mat0005365*, vol. 2, Feb. 26, 2001.

"Decomposition of Heartbeat Time Series; Scaling Analysis of the Sign Sequence;" Y Ashkenazy, et al; *Los Alamos arXiv;cond–mat/0102481*, Feb. 27, 2001.

"Discrimination Between Healthy and Sick Cardiac Autonomic Nervous System by Detrended Heart Rate Variability Analysis;" Y.C Ashkenazy, et al; *Los Alamos arXiv:chao-dyn/9810008*; vol. 2, Oct. 13, 1998.

Abstract: "Lyapunov Exponents as a Dynamical Indicator of a Phase Transition;" Julien Barre, et al; *Europhysics Letters* 55, 154 (2001).

"Variational Properties of Multifractal Spectra;" Luis Barreira; *Nonlincarity* 14 (2001), 259–274.

"A Non–Additive Thermodynamic Formalism and Applications to Dimension Theory of Hyperbolic Dynamical Systems;" Luis M. Barreira; *Ergodic Theory Dynam. Systems 16* (1996), 871–927.

"Dimension and Product Structure of Hyperbolic Measures;" Luis Barreira, et al; *Annals of Mathematics*, 149 (1999), 755–783.

"Non–Extensive Statistical Mechanics Approach to Fully Developed Hydrodynamic Turbulence;" Christian Beck; *Los Alamos arXiv:cond–mat/0005408*, vol. 1, May 24, 2000.

Abstract: Non–Extensive Statistical Mechanics and Particle Spectra in Elementary Interactions; Christian Beck; *Physica*; A286 (2000) 164–180.

Abstract: "Dynamical Foundations of Nonextensive Statistical Mechanics;" Christian Beck; *Cond–Mat/0105374*; May 18, 2001.

Van Den Berg, J.C., et al; *Wavelets in Physics*; Aug. 19, 1999.

"Scale Invariance in the Nonstationarity of Physiological Signals;" Pedro Bernaola–Galvan; *Los Alamos arXiv.cond-mat/0005284*; vol. 2, Jay 22, 2000.

"Mimicking a Turbulent Signal: Sequential Multiaffine Processes;" L. Biferale; *Los Alamos arXiv:chao-dyn/9711006*; Nov. 3, 1997.

"Apparent Mulifractality in Financial Time Series;" J.P. Bouchaud; *The European Physical Journal B*; 13, 595–599 (2000).

"Scaling Transformation and Probability Distributions for Financial Time Series;" Mar–Etienne Brachet; *Los Alamos arXiv:cond–mat/9905169*; May 12, 1999.

Abstract: *Fractals in Science*; Armin Bunde; 1994.

"A Unified Grand Canonical Description of the Nonextensive Thermostatistics of the Quantum Gases; Fractal and Fractional Approach;" F. Buyukkhic; *The European Physical Journal B*; 14, 705–711 (2000).

"Self–Similarity of the Plasma Edge Fluctuations;" B.A. Carreras; *Physics of Plasmas*; vol. 5, No. 10, Oct. 1998, 3632–3643.

"Long–Range Time Dependence in the Cross–Correlation Function;" *Physics of Plasmas*; vol. 6, No. 2, Feb. 1999, 485–494.

"Self–Similarity Properties of the Probability Distribution Function of Turbulence–Induced Particle Fluxes at the Plasma Edge;" B.A Carreras; *Physical Review Letters*; vol. 83, No. 18, Nov. 1, 1999, 3653–3656.

Abstract: "Power–Law Sensitivity to Initial Conditions within a Logistic–Like Family of Maps: Fractality and Nonextensivity;" U.M.S. COSTA; *Los Alamos cond–mat/9701096*.

"Wavelet Based Fractal Analysis of Airborne Pollen;" M.E. Degaudenzi; *Los Alamos arXiv:adap–org/9808004*, Aug. 27, 1998.

"Multscaling Analysis of Fractals and Turbulent Signals Using the Wavelet Transform;" Thomas Fishcer; Institute for Computer Applications, University of Stuttgart, Germany.

"Effects of Head–Down Bed Rest on Complex Heart Rate Variability: Response to LBNP Testing;" Al Goldberger; *J. Appl Physiol*; (Dec. 1994) 77(6):2863–9.

"Application of Statistical Physics to Heartbeat Diagnosis;" S. Havlin, et al; *Physica A*; 724 (1999) 99–110.

"Pesin Theory; " M. Hazewinkel; *Encyclopaedia of Mathematics*; Supplement vol. 1, 1997, 406–411.

"An Entropy Primer;" Chris Hillman; May 21, 1996.

"What is Information?;" Chris Hillman; Jul. 7, 1995.

"All Entropies Agree for an SFT;" Chris Hillman; Feb. 18, 1998.

"Stochastic Feedback and the Regulation of Biological Rhythms;" Plamen CH. Ivanov; *Los Alamos arXiv:cond-mat/9710325*; Oct. 29, 1997.

"Sleep–Wake Differences in Scaling Behavior of the Human Heartbeat: Analysis of Terrestrial and Long–Term Space Flight Data;" P. CH. Ivanov; *Europhysics Letters*; 48 (5) (1999) 594–600.

Abstract PubMed: "Scaling Behavior of Heartbeat Intervals Obtained by Wavelet–Based Time–Series Analysis;" Ivanov PC.

"Multifractal Formalism for Functions Part I: Results Valid for all Functions;" S. Jaffard; *Siam J. Math. Anal.*, vol. 28, No. 4, Jul. 1997, 944–970.

"Mulifractal Formalism for Functions Part II: Self–Similar Functions;" S. Jaffard; *Siam J. Anal.;* vol. 28, No. 4 Jul. 1997, 971–998.

"q–Calculus Framework For Entropy In Multifractal Distributions; " Ramandeep S. Johal; *Los Alamos cond–mat/9803017*; Mar. 2, 1998.

Abstract: "Non–linear Dynamics and Scale–Invariance in the Heart Rate Variability;" Kalda, J.

Abstract: "Chais, Ergodicity, and the Thermodynamics of Lower–Dimensional Hamiltonian Systems;" Henry E. Kandru?; *Astro–ph/0108038*.

"Generalization to Nonextensive Systems of the Rate of Entropy Increase: The Case of the Logistic Map;" Vito Latora; *Los Alamos cond–mat/9907412*; Vo. 2, Aug. 31, 1999.

"Second–Order Self–Similar Identities and Multifractal Decompositions;" Ka–Sing Lau.

Abstract: "A Hamiltonian Formulation for the Diffusion Equation;" Lewalle, J.; *Physical Review E*, 55 (1997), 1590–1599.

Nonextensivity and Multifractality in Low–Dimensional Dissipative Systems;: M.L. Lyra; *Los Alamos arX8v:cond–mat/9709226*, vol. 1, Sep. 20, 1997.

Abstract: "Heart Rate Dynamics Before Spontaneous Onset of Ventricular Fibrillation in Patients with Healed Myocardial Infarcts;" Makikallio, TH, *Am J Cardiol*, Mar. 15, 1999, 83(6)880–4.

"Convergence to the Critical Attractor of Dissipative Maps: Log–Periodic Oscillations, Fractality and Nonextensivity;" F.A.B.F. De Moura; *Los Alamos arXiv:cond–mat/0002163*; vol. 1, Feb. 10, 2000.

Abstract: "Hamilton–Jacob Formulation of KS Entropy for Classical and Quantum Dynamics," M. Hossein Partovi.

"Numerical Estimates of Generalized Dimensions D(q) for Negative q;" Romuadlo Pastor–Satorras.

"Cardiac Interbeat Interval Dynamics From Childhood to Senescence;" Sirkku M. Pikkuijamsa; *Circulation*, Jul . 27, 199, 393–99.

"An Improved Multifractal Formalism and Self–Similar Measures;" Rolf Ried; *Journal of Math Analysis and Applications* 189, 462–490 (1995).

"Introduction of Multifractals;" Rudolf H. Riedi; Sep. 5, 1999.

"A Fast Algorithm for Generating Long Self–Affine Profiles," Ingve Simonsen, et al.; *Los Alamos cond–mat/9909055*, Sep. 3, 1999.

"Determination of the Hurst Exponent by use of Wavelet Transforms," Ingve Simonsen, et al.; *Los Alamos cond–mat/97071532*, vol. 2, Feb. 6, 1998.

Abstract: Pub Med; "Levy Flights from a Continuous–Time Process," Sokolov Im.

"Statistical Physics and Physiology: Monofractal and Multifractal Approaches," H.E. Stanley, et al.

"Local Effective Holder Exponent Estimation on the Wavelet Transform Maxima Tree;" Zbigniew R. Struzik.

The Wavelet Transform in the Solution to the Inverse Fractal Problem;: Zbigniew R. Struzik, *Fractals*, vol. 3, No. 2 1995.

"Wavelet Transform in Similarity Paradigm," Zbigniew R. Struzik, et al.

"Determing Local Singularity Strengths and their Spectra with the Wavelet Transform," Zbigniew R. Struzik, *Fractals*, vol. 8, No. 2 (2000).

"Determining Local Singularity Strength and its Spectrum with the Wavelet Transform," Zbigniew R. Struzik.

"Fractals under the Microscope," Zbigniew R. Struzik.

"Cumulative Effective Holder Exponent Based Indicator for Real–Time Fetal Heartbeat Analysis During Labour," Zbigniew R. Struzik, *World Scientific*, Jun. 25, 2001.

"Wavelet Transfrom in Similarity Paradigm II," Z.R. Struzik, et al., *INS–R9815*, Dec. 31, 1998.

"Wavelet Transform in Similarity Paradigm I," Z.R. Struzik, et al., *INS–R9802*, Jan. 31, 1998.

"Removing Divergences in the Negative Moments of the Multi–Fractal Partition Function with the Wavelet Transformation," Z.R. Struzik, *INS–R9803*, Jan. 31, 1998.

"Revealing Local Variability Properties of Human Heartbeat Intervals with the Local Effective Holder Exponent," Z.R. Struzik, *INS–R0015*, Jun. 30, 2000.

Abstract: "Outlier Detection and Localisation with Wavelet Based Multifractal Formalism," Z.R. Struzik, *CWI Report*.

"Multifractal Analysis of Dimensions and Entropies," Floris Takens, et al.

"Heart Rate Variability: Measures and Models," Malvin C. Teich, et al.; *Los Alamos arXiv:physics/0008016*, Aug. 7, 2000.

"ROC Analysis and a Realistic Model of Heart Rate Variability," Stefan Thurner, et al., *Los Alamos arXiv:chao–dyn/9806022*, Jun. 19, 1998.

"Receiver–Operating–Characteristic Analysis Reveals Superiority of Scale–Dependent Wavelet and Spectral Measures for Assessing Cardiac Dysfunction," Stefan Thurner, et al., *Los Alamos physics/9901007*, Jan. 8, 1999.

"Multiresolution Wavelet Analysis of Heartbeat Intervals Discriminates Healthy Patients from those with Cardiac Pathology," Stefan Thurner, et al., *Los Alamos arXiv.adap–org/9711003*, Nov. 26, 1997.

"Conservation Laws in Coupled Multiplicative Random Arrays Lead to 1/f Noise," Stefan Thurner, et al., *Los Alamos arXiv:adap–org/9709005*, Sep. 30, 1997.

"Circular–Like Maps: Sensitivity to the Initial Conditions, Multifractality and Nonextensivity," Ugar Tirnakh, et al., *Los Alamos arXiv?cond–mat/9809151*, vol. 1, Sep. 10, 1998.

"Entropic Nonextensivity: A Possible Measure of Complexity," Constantino Tsallis, *Los Alamos arXiv:cond–mat/0010150*, vol. 1, Oct. 10, 2000.

Abstract: Pub Med, "Effects of Pharmacological Adrenergic and Vagal Modulation on Fractal Heart Rate Dynamics," Tulppo MP, et al., *Clin Physiol* Sep. 2001; 21(5): 515–23.

Abstract: "Connection Between Energy–Spectrum Self–Similarity and Specific Heat Log–Periodicity," R.O. Vallejos, et al.

"Multi–Affine Analysis of Typical Currency Exhange Rates," N. Vandewalle, et al., *European Physical Journal B* 4, 257–261 (1998).

"A Statistical Test for the Time Constancy of Scaling Exponents," Darryl N. Veitch.

"Generalized Entropies in Dynamical Systems," Evgeny Alexandrovich Verbitskiy, Apr. 21, 1974.

Abstract: PubMed, "Deviations from Uniform Power Law Scaling in Nonstationary Time Series," Viswanathan GM, et al.

* cited by examiner

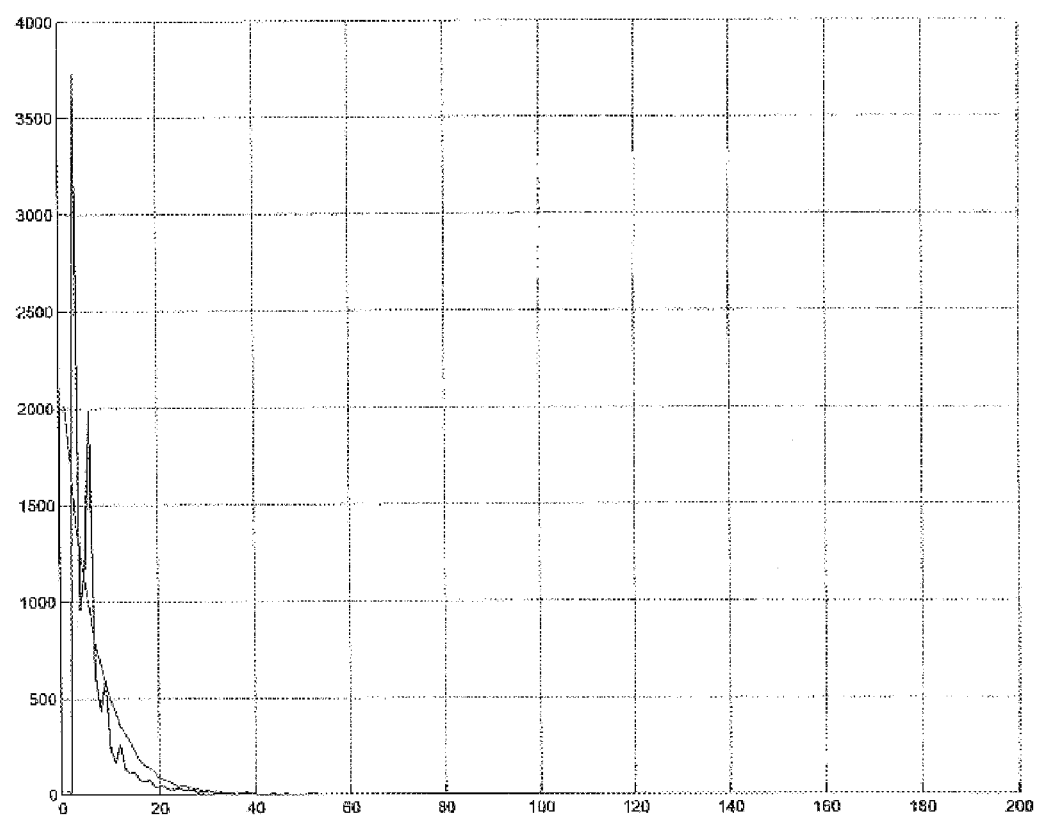
Fig. 7a₁

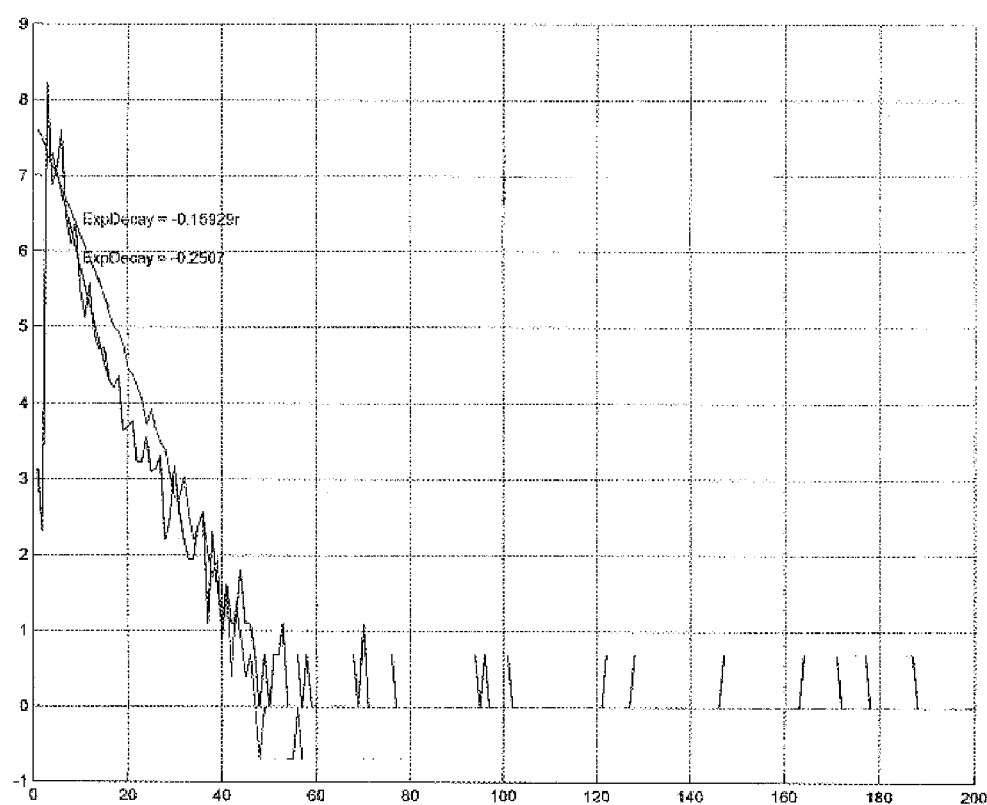
Fig. 7a₂

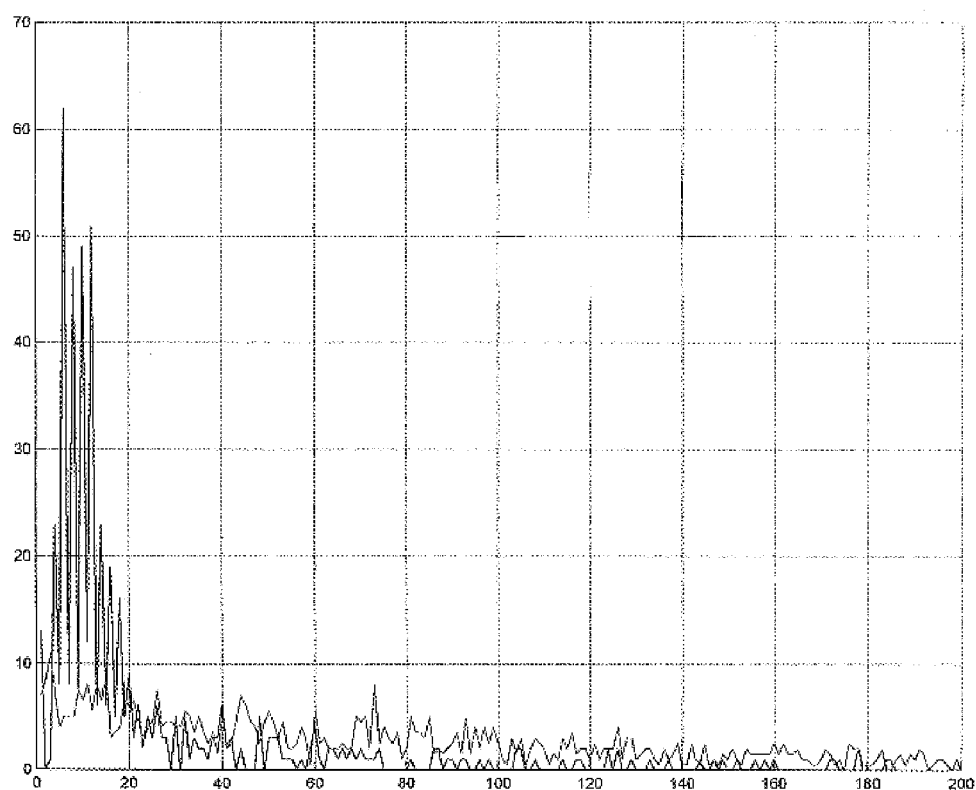
Fig. 7b₁

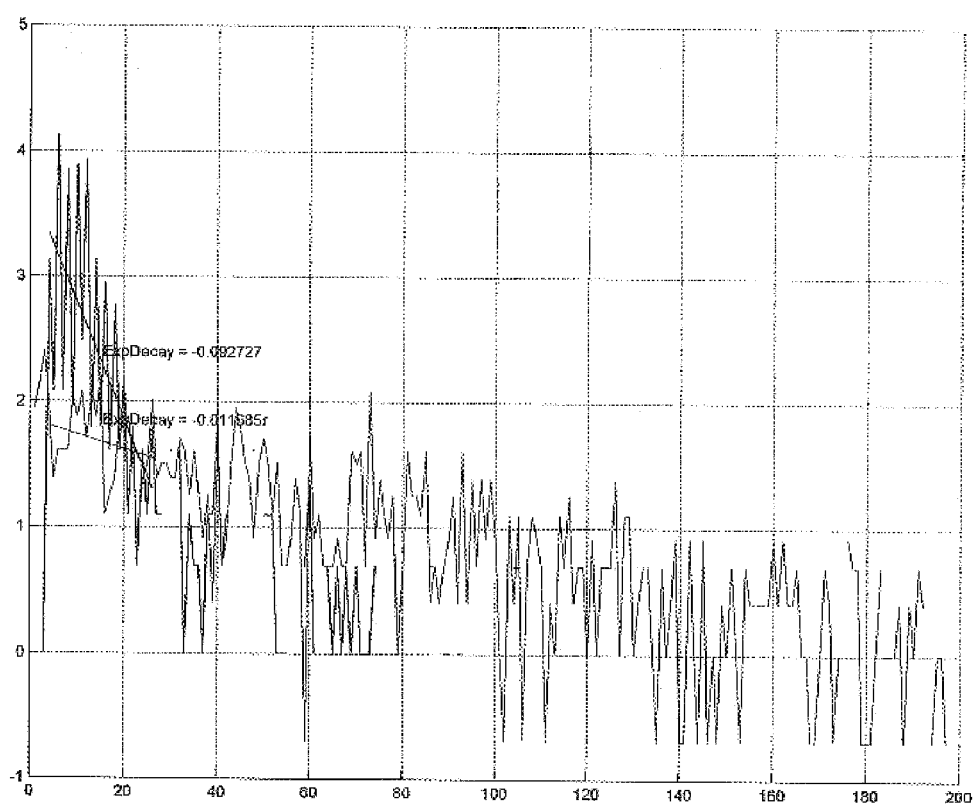
Fig. 7b$_2$

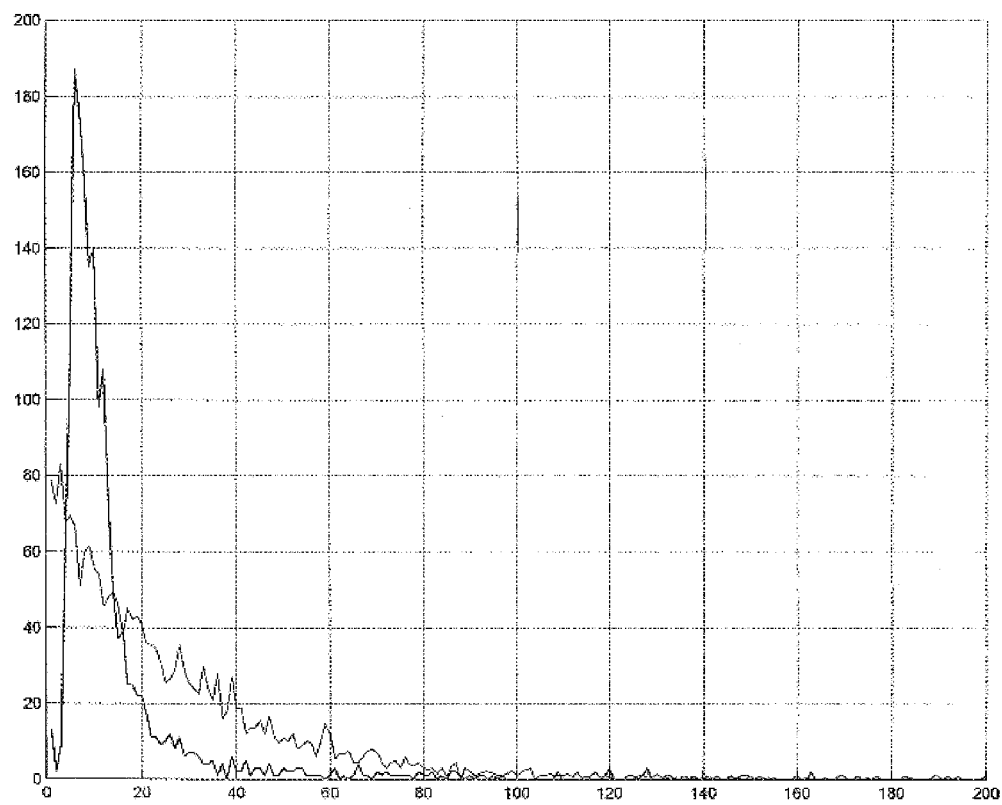
Fig. 7c₁

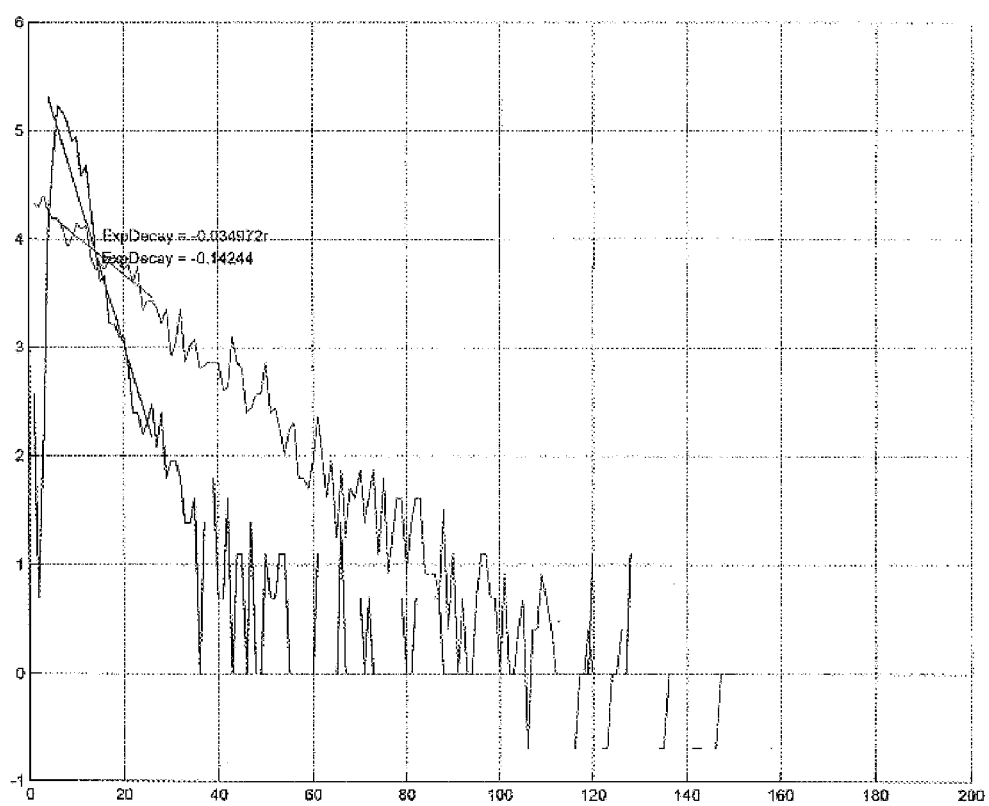
Fig. 7c₂

METHOD FOR DIAGNOSING HEART DISEASE, PREDICTING SUDDEN DEATH, AND ANALYZING TREATMENT RESPONSE USING MULTIFRACTAL ANALYSIS

BACKGROUND OF THE INVENTION

The present invention is directed to a battery of multifractal-based tests developed for the analysis of electrocardiogram (EKG) data. The invention is preferably for clinical use in a novel integrated approach to diagnosis of heart disease, prognosis of cardiac conditions, and monitoring of heart disease therapies. This multifractal approach is not available with current, clinically available cardiographic methods.

Cardiovascular disease currently affects approximately 20 million Americans. Roughly 12 million Americans are affected by coronary artery disease (CAD), and 5 million suffer from congestive heart failure (CHF). More importantly, millions suffer from undiagnosed heart disease; the prevalence of undiagnosed CHF is estimated to be approximately 20 million in the U.S. In addition, 400,000 Americans with CAD or CHF die from sudden cardiac death each year. Although there are a number of conventional nonfractal tests for the diagnosis of heart disease (several of them highly invasive), none of these tests can effectively predict which patients in this group of 17 million (CAD+CHF) are at risk of sudden death. Since it is impractical and undesirable to treat every person with heart disease (CAD or CHF) as if such a person were at risk for sudden death, a reliable predictive test (or test battery) to determine which patients are at high risk would be of great value.

In addition, new drugs and other treatments continue to be developed to treat heart disease. There are, however, no currently available analytic test regimens to rapidly evaluate how well the patient may respond to treatment and whether the risk of sudden death has been decreased by anti-arrhythmic therapy. As a result, the efficacy of these treatments must be determined empirically with slow, multi-year, prospective-controlled studies, which are very difficult to extrapolate to each individual patient. Therefore, an analytic method that would monitor a patient for signs of potential improvement on therapy would also be of great value. The diagnosis of CAD and CHF would also be greatly improved by a very sensitive and specific but noninvasive test to replace or supplement expensive and invasive modalities like heart catheterization and allow screening of patients with asymptomatic heart disease.

Over the last decade, considerable promise has been demonstrated in this field by the application of one-dimensional fractal time series analysis methods to RR-interval EKG data. Fractal scaling techniques have been employed to demonstrate that the human heart beat has fractal scaling characteristics, and that this was altered by disease. These analyses used relatively simple techniques to analyze the fractality, which may be termed "monofractal" analysis. Most clinical EKG studies utilized pre-wavelet technology, Detrended Fluctuation Analysis (DFA) for analysis of short term (<11 beat) or intermediate to long term (>11 beat) monofractal scaling analysis. We will subsequently describe >11 beat (long term) analyses in the literature as LTAlpha, and <11 beats (short term) analyses as STAlpha. These early studies have revealed clinical interpretations never before seen in conventional methods of EKG analysis, permitting some limited degree of differentiation between patients with heart disease and those without.

DFA analysis has also shown that patients with congestive heart failure (CHF) have an elevated DFA LTalpha scaling coefficient when compared with normals. These abnormalities tended to normalize at night within a few hours, as would be expected from a physiologic standpoint. Other researchers have noted a similar LTalpha diurnal rhythm in normal subjects.

More recently, several authors have noted the prognostic and diagnostic value of the STalpha scaling coefficient. A prospective study of 69 heart failure patients showed that the short term DFA STalpha revealed diagnostic information not extractable from traditional methods of heart variability analysis. This study is described in K.K.L. Ho et al., "Predicting Survival in Heart Failure Case and Control Subject by Use of Fully Automated Methods for Deriving Nonlinear and Conventional Indices of Heart Rate Dynamics," Circulation 1997;96:842–848, which is incorporated herein by reference. A separate study examined STalpha analysis of three groups of 45 patients each: (1) normals, (2) post myocardial infarction (post-MI) with ventricular tachycardia (v-tach) or electrically inducible v-tach, and (3) post-MI without v-tach or electrically inducible v-tach, revealing that the STalpha was significantly reduced in the post-MI v-tach group. This suggested that the STalpha reduction may be related to vulnerability to v-tach. This study is described in T. H. Makikallio et al., "Dynamic Analysis of Heart Rate May Predict Subsequent Ventricular Tachycardia after Myocardial Infarction," American Journal of Cardiology Sep. 15, 1997;80(6):779–83. The STalpha was also studied in 38 patients with stable angina, but no prior MI or meds against 38 control subjects, and was shown to be a better predictor than other heart rate variability parameters. This work is described in T. H. Makikallio et al., "Heart Rate Dynamics in Patients with Stable Angina Pectoris and Utility of Fractal and Complexity Measures," American Journal of Cardiology Jan. 1, 1998;81(1):27–31. A follow-up study of 414 post-MI patients with depressed contractility or ejection fraction (EF) of 35% showed that a reduced STalpha was the most powerful predictor of mortality of all available statistical EKG analytic methods. This work is described in H. V. Huikuri et al., "Fractal Correlation Properties of R—R Interval Dynamics and Mortality in Patients with Depressed Left Ventricular Function after an Acute Myocardial Infarction," Circulation 2000;101:47–53. A 4-year, prospective study of 159 patients with 35% EF post-MI showed that a reduced STalpha was the best predictor of mortality; this work is described in T. H. Makikallio et al., "Fractal Analysis of Heart Rate Dynamics as a Predictor of Mortality in Patients with Depressed Left Ventricular Function after Acute Myocardial infarction. Trace Investigators. TRAndolapril Cardiac Evaluation," American Journal of Cardiology Mar. 15, 1999;83(6):836–9. Another Danish study followed 499 patients with CHF and EF of <35%. During a followup period of 665 days, and after adjusting for age, functional class, medication, and EF, a reduced short-term alpha remained an independent predictor of mortality, RR 1.4 (95% Cl 1.0–1.9, P<0.05). This result is described in T. H. Makikallio et al., "Fractal Analysis of Time- and Frequency-Domain Measures of Heart Rate Variability as Predictors of Mortality in Patients with Heart Failure," American Journal of Cardiology Jan. 15, 2001;87 (2):178–82. Lastly, a wavelet based (non-DFA) STalpha analysis revealed that in 428 post-MI patients with 105 controls studied over a 2000-day period, the STalpha had the best Kaplan-Meyer survival statistics, when compared to other EKG based statistical tests. This work is described in Y. Ashkenazy et al., "Scale Specific and Scale Independent Measures of Heart Rate Variability as Risk Indicators," Los Alamos arXiv:physics/9909029 Sep. 17, 1999. Hence, it is reasonable to conclude that a decreased STalpha fractal scaling coefficient has diagnostic value in predicting risk of sudden death.

Other work has demonstrated the clinical value of the DFA STalpha in monitoring response to drug therapy, and prediction of runs of abnormal beats from atrial fibrillation. A STalpha study of the effect of Atenolol therapy in advanced CHF patients revealed changes after three months, but other statistical EKG parameters and intermediate to LTalpha did not change This study is described in L. Y. Lin et al., "Reversal of Deteriorated Fractal Behavior of Heart Rate Variability by Beta-Blocker Therapy in Patients with Advanced Congestive Heart Failure," Journal of Cardiovascular Electrophysiology Jan. 12, 2001 (1):26–35. A study of patients at risk for spontaneous atrial fibrillation revealed that both approximate entropy (ApEn) and STalpha decreased approximately 20 minutes before atrial fibrillation, but traditional heart variability methods did not, as described in S. Vikman et al., "Altered Complexity and Correlation Properties of R—R Interval Dynamics before the Spontaneous Onset of Paroxysmal Atrial Fibrillation," Circulation 1999;100:2079–2084. This raises the possibility that STalpha measures a fundamental property of cardiac function, as low values of STalpha correlate with poor survival in Ml patients with low EF, and may predict risk of atrial fibrillation.

A newer, more powerful method of fractal analysis termed wavelet-based multifractal analysis has recently been applied to EKG data. We call this type of analysis multifractal (MF) Holder analysis herein, although earlier works may often use the Hurst coefficient interchangeably with the related Holder coefficient. The MF Holder analysis of human EKGs was described by a Boston University team in P. C. Ivanov et al., "Multifractality in Human Heartbeat Dynamics," Nature Vol. 399, pp. 461–465 (1999), which is incorporated herein by reference. This team examined the multifractal scaling properties of EKG RR intervals for intervals >16 beats, roughly equivalent to the DFA LTalpha analysis described above. Unlike the earlier DFA (high-pass filter type) monofractal analysis, the analysis is performed in more sophisticated, narrowly defined wavelet bands. A spectrum of local fractal scaling coefficients is generated for each time series snapshot analyzed, enhancing the potential richness of the data analysis. This continuum of scaling coefficients generates new parameters not available with monofractal EKG time-series analysis. No information is lost by this analysis, because if the signal is truly monofractal, the analysis reduces to the monofractal situation.

The Boston University analysis also revealed that the fractal pattern of the human heartbeat was much more complex than previously described. The authors concluded that the EKG data in congestive heart failure (CHF) patients was monofractal, and the normal control subjects were multifractal. These observations are crucial to the fractal analysis of EKG time series, indicating that the previously described monofractal analysis may be inadequate in characterizing the richness of the fractal behavior of the human EKG, and in detecting heart disease with a high sensitivity. Furthermore, this multifractal analysis may also offer new diagnostic features not appreciated in the monofractal methods. It is our belief that the degree of multifractality of the healthy heartbeat reflects the healthy cardiac system's greater adaptability to change, and that the loss of multifractality in heart disease is associated with failure to adapt to the external environment.

The same Boston University group also analyzed the effect of nerve control mechanisms of the heart on the multifractal nature of the human heartbeat in L. A. N. Amaral, et al., "Behavioral-Independent Features of Complex Heartbeat Dynamics," Los Alamos arXiv:cond-mat/0106508 v1 Jun. 25, 2001 (originally published at Physical Review Letters Vol. 86, No. 26, pp. 6026–6029 (2001)), which is incorporated herein by reference. The group was able to show that blockade of sympathetic and parasympathetic nerve input into the heart by drugs significantly decreased the level of multifractal complexity.

A critical limitation of the multifractal analysis described above is that the Boston University group only pre-filtered aberrant beats up to a maximum of 2% of the total time series, and the <16 beat scaling region was excluded. We have discovered, however, that (1) 11 out of 47 of the heart disease patients we studied have 5% or more abnormal beats; (2) these beats can adversely affect the MF Holder coefficient; and (3) these beats falsely elevate our multifractal cascade coefficient MFCC (described below). These abnormalities are not seen in our 12 normal control patients, and are not removed by the pre-filtering method described in this prior art. Examination of representative "raw" RR-interval data can be very impressive in patients with such abnormal beats, as a well-defined heart rate may not be evident unless 8- or more beat smoothing is performed first.

The presence of the abnormal or arrhythmic beats appears to generate a phenomenon called intermittency, namely that the fractal behavior of the time series is disrupted by the presence of abnormal beat events. The prior art prefiltering methods as described herein consist of removing 2% or less abnormal beats. In most cases this is done by removing (prefiltering) the RR-interval beats that exceed so many standard deviations from a reference value, often based on a 5–10 beat moving average, so that the outliers can be identified. The 2% prefiltering limit consensus is apparently based on the assumption that more abnormal beats could cause distortion of the MF Holder scaling coefficient, or other fractal scaling coefficients such as the ST DFA alpha, or LT DFA alpha. We have also discovered that as little as a 1% incidence of abnormal beats can adversely affect the multifractal scaling coefficient if they are tightly clustered in time. Prior art anomalous beat filtering methods will not work in this situation, as the clustered abnormal beats could represent 10% or more of the fractal signal in some regions of the RR-beat series.

In summary, the prior art methods of removing abnormal beat intermittency effects may not work in patients with 2% or more abnormal beats, or in other situations where the abnormal beats are clustered in time. As we have discovered, these abnormal beats are quite common in clinical practice. Thus a practical method for (1) detecting abnormal beats, (2) detecting the presence of beat clustering, and (3) removing the sequelae of these abnormal beats is needed.

Still another limitation of the prior art is that there is no formal attempt to quantify the multifractal nature of the human heartbeat. Healthy patients were described as being multifractal, and heart disease patients as monofractal, but this information was not quantified. We have found that in the real world of clinical practice, some degree of multifractality is always present, although it is more prominent in some patients than in others.

Lastly, the MF Holder approach has to date only been applied to the LT (long term) >16 beat scaling region. Each of these limitations of the prior art are overcome by the present invention as described below.

SUMMARY OF THE INVENTION

The present invention comprises one or more of a battery of tests based on multifractal analysis and applies them to EKG data to produce an integrated, noninvasive diagnostic/prognostic approach. Useful results from these tests can be made available in 15 minutes or less (multifractal alpha [MF alpha]) to several hours (MF Holder, or MF Cascade Coefficient [MFCC]). A multifractal version of the ST alpha scaling coefficient (our MFAlpha) and a multifractal version of the LT alpha (our MFHolder) offer additional useful information about cardiac disease. Improved sensitivity and specificity is achieved with the multifractal methods described below because they lead to a more sophisticated, detailed measurement of fractality. Our studies with 32 CHF patients and 12 normal controls reveal that our MF alpha has a perfect receiver operating curve (ROC), representing a significant improvement over similar analyses from the prior art using the monofractal DFA STalpha or wavelet ST alpha. Certain important aspects of various embodiments of the present invention will be described in summary below.

First, certain embodiments of the invention comprise the addition of a wavelet smoothing step to the EKG data prior to the application of multifractal Holder analysis. This method minimizes the intermittency effect of abnormal/arrhythmic beats by removing scales not analyzed, but with minimal signal distortion. We have found that this step is generally necessary in our patient population. Our analysis demonstrated that abnormal beats are quite common in our 32 CHF and 15 CAD patients, with 11 patients having more than 5% abnormal beats. This high percentage of abnormal beats is too great to be removed by prior art methods. In a preferred embodiment, we use the MODWT Daubechies 8-beat discrete wavelet transform filter. This discrete wavelet transform is very fast, and has the desired property of precisely preserving the time dependence of the EKG time series to be analyzed, while only removing scaling segments of the time series outside the scaling region to be analyzed. By the use of this smoothing process, no phase-shift or amplitude-type artifacts are introduced into the results, and the only change to the data is the selective removal of features in the fractal scales excluded from the MFA. This smoothing step also allows us to apply the MF Holder method to patients with a significant percentage of confounding abnormal beats, with a significant gain in CHF diagnostic sensitivity and specificity, from 63% and 69%, respectively, to 82% and 75%, respectively. Thus the present invention represents a significant improvement over existing MFA techniques, making MFA applicable to a much larger patient population, even when abnormal/arrhythmic beats are present.

Second, certain embodiments of the present invention include measurement of the MF Holder coefficient, which is determined by multifractal analytic methods through analysis of the continuous wavelet transform (CWT) of the EKG RR-interval series. The multifractal approach to EKG RR interval series analysis appears necessary, as the Human EKG is generally not monofractal. The multifractal cascade generates a family of Holder coefficients, rather than a single Holder scaling coefficient. A variety of other parameters in addition to the MF Holder coefficient can be derived from the basic MF analysis, some of which are outlined herein as having application in cardiac analysis. A variety of other parameters in addition to the MF Holder coefficient can be derived directly from the basic MF analysis, some of which are outlined elsewhere. These include Shannon entropy, several kinds of multifractal entropy, Kolmolgorov-Smirnoff entropy, Lyupanov exponents, and Tsallis entropic scaling.

Third, certain embodiments of the present invention comprise a method to quantify the multifractality of the EKG time series, in addition to the MF Holder scaling coefficient measurement. This method utilizes a quadratic equation to model the multifractal cascade—describing the multifractal process with a single coefficient—which we called multifractal cascade coefficient (MFCC). We have determined empirically that a quadratic fit is an unusually good approximation in most cases where a multifractal cascade is evident. Exceptions include "phase changes" where the multifractal cascade is not defined (these are ignored), and where the time series is highly monofractal. In the monofractal case, the fit is not as precise, but the deviation from multifractality is still determined qualitatively.

Fourth, the application of our multifractal analysis has the unexpected side benefit of reducing the minimum size of the EKG time series snapshot required for fractal analysis. This may be due to the increased analytic detail offered by the multifractal analysis. In a preferred embodiment, the snapshot size may be readily reduced to 2048 beats without increase in statistical uncertainty when compared to other less sophisticated (monofractal) methods, where 4098 beats or more may be necessary. We can overlap multifractal snapshots as much as 16 times with an additional reduction in sampling error by a factor of two or more. This new improved analysis leads to useful time series information on a EKG time series of only 2 hours in length, with time resolution of less than 15 minutes even with a 2048-beat snapshot. Thus our MF Holder technique can now routinely examine the time series dependence of a variety of MF parameters in an EKG recording, permitting comparison with time of day, current heart rate, time of drug therapy, or any other measurable parameter, such as PO2, cardiac output, or blood pressure. This greatly increases the utility of this invention in screening/treatment of heart disease in a clinical setting.

Fifth, certain embodiments of the present invention comprise the development, validity testing, and application of our ST multifractal alpha coefficient (MF alpha). We applied MF mathematical methodology to the 1–4 beat scaling region we found optimal after our monofractal alpha scaling analysis, which was based on the same CWT wavelet analysis of the EKG RR-interval snapshots we used with our MF Holder analysis. The MF alpha method is altered in that the MF analysis is ignored for negative values of q, and that the "sup" method used in the MF Holder analysis is not needed. A MF alpha cascade is not defined due to the limitations of the method. We determined that the MF Holder coefficient for q=2 is the MF alpha analogue, and validated our new MF alpha by comparison with our old monofractal alpha, analyzing all 47 (32 CHF and 15 CAD) patients and 12 controls. Our age-matched analysis of CHF and normal subjects indicates that our MF alpha performs with 100% sensitivity and 100% specificity in diagnosing CHF patients, when an appropriate critical MF alpha threshold is chosen. This is a significant improvement over the reported monofractal alpha analysis performed by others as described above. This method also offers improved statistical performance over monofractal STalpha methods, and overlapping snapshots give the additional statistical benefit seen with MF Holder analysis. Since snapshot sizes less than 64 beats can be used, raw data collection can be quite rapid with our MF alpha method, a desirable goal for rapid cardiology clinic applications. We also believe that the MF alpha may demonstrate significant prognostic value, based on the prior monofractal ST alpha work noted above, which has shown the powerful predictive/diagnostic value of DFA STalpha and wavelet STalpha.

Sixth, certain embodiments of the present invention comprise the addition of an abnormal beat cluster analysis detection step prior to other MF analyses of EKG data. This accomplishes two things: first, it enables detection of the abnormal arrhythmic beats, which can generate an intermittency effect as noted above. This process adversely affects the (long term) MF Holder, but not our (short term) MF alpha analysis. The multifractal cascade (our MFCC) is even more seriously affected by broadening of the cascade. Second, we may determine the presence of abnormal beat clustering. The detection of abnormal beat clustering appears very important, as this phenomenon can worsen the disrupting effect of a fixed percentage of abnormal beats. The two numbers derived from our abnormal beat cluster detection algorithm—namely the percentage of abnormal beats, and the degree of clustering—give a measure of the confidence one can have in the unsmoothed MF Holder analysis, and how much additional smoothing might be needed. The preferred embodiment of our abnormal beat cluster analysis uses a mathematical technique known as "Levy flight" analysis.

We believe that a clustering of abnormal/arrhythmic beats presents a much greater risk of sudden death than a similar number of abnormal beats spread over the entire 24-hour time period typically analyzed. This premise is supported by our preliminary analysis, which reveals that 4 out of 47 heart disease (CHF and CAD) patients have very abnormal beat clustering, but all with <5% abnormal beats. There are, however, 11 out of 47 heart disease patients analyzed with >5% abnormal/arrhythmic beats, and none of these patients have abnormal beat clustering. We believe that the implication is therefore that severe beat clustering combined with >5% abnormal beats may not be compatible with survival. Hence, our beat cluster analysis may provide a powerful tool to predict risk of sudden death in patients with heart disease.

Seventh, our sequential discrete wavelet smoothing analysis step used to remove the abnormal beats can be used to identify those patients whose MF Holder coefficient is sensitive to the degree of smoothing (outside the fractal scaling range to be analyzed). The data for individuals without abnormal beats is not significantly affected by the smoothing step, but the data for those with abnormal beats is usually (but not always) affected. Consequently, we can use the dependence of the MF Holder analysis on sequential beat smoothing to further classify the patients we study. Our belief is that patients whose Holder coefficient rises steadily with sequential smoothing (relative to normal controls), but not rising enough to generate an abnormal Holder coefficient, may have suspect MF Holder coefficients due to incomplete removal of abnormal beats. The true MF Holder coefficient may therefore be higher in these patients. Hence the rate of change in MF Holder with sequential wavelet smoothing may also be of value as a diagnostic test for heart disease.

Eighth, certain embodiments of the present invention comprise the use of alternative methods to eliminate abnormal beat intermittency. A probability distribution function (PDF) approach should offer a different perspective from conventional MF Holder analysis, since one can determine the MF Holder directly from a self-similarity scaling formula, without calculating the MF cascade. We believe that the PDF approach will be effective at separating healthy and heart disease patients even in the presence of a significant number of abnormal beats. These beats distort the EKG time series by creating a long tail on the PDF distribution, but the body of the PDF distribution is less affected. Thus if the MF Holder coefficient is determined only by the self-similar scaling of the body of the PDF distribution, the distorting effect of abnormal/arrhythmic beats can be minimized. Other approaches to the abnormal beat problem consist of the selective removal of the intermittent wavelet ridges, or direct calculation of the Holder coefficient and MF cascade.

Ninth, the invention comprises the calculation of several types of multifractal entropy, Lyapunov exponents, and Tsallis entropic scaling coefficients. These parameters can all be calculated directly from the MF Holder analysis in a mathematically rigorous fashion. Since Approximate Entropy (ApEn) is thought to be of clinical value in estimating the complexity of an EKG series, it is believed that these additional parameters may be of greater utility in the diagnosis, therapy, and prognosis of cardiac conditions.

An overall goal of the present invention is to utilize a multivariant approach to the multifractal analysis of Human EKG RR-interval series for clinical application, beginning with methods least affected by abnormal/arrhythmic beats. In a preferred embodiment, we begin the analysis with our "Levy flight" cluster analysis, which determines the presence and number of abnormal beats in the series analyzed, and the existence of abnormal beat clustering. We then calculate (1) our short-term MF alpha coefficient, which has an initial 100% sensitivity and 100% specificity in separating heart disease patients from normal ones; (2) our MF Holder coefficient with wavelet-based, pre-analytic smoothing to remove the short beat intervals of less than 8 beats, (since abnormal/arrhythmic beats can adversely affect the Holder analysis); (3) our sequential wavelet smoothing steps to document dependence of the MF Holder coefficient on same; (4) and lastly our multifractal cascade coefficient (MFCC) to quantify the degree of multifractality. This stepwise approach enables wide use of our method in heart disease patients for screening, prognosis and prediction of therapeutic response. Given the depth and variety of our multifractal diagnostic approach to analysis of human EKGs, we anticipate that this battery of tests will be useful to screen the general population for the presence of heart disease.

These and other features, objects, and advantages of the present invention will become better understood from a consideration of the following detailed description of the preferred embodiments and appended claims in conjunction with the drawings as described below:

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2a is a graph illustrating the EKG RR-interval series results for a patient with only 1% abnormal beats, where the anomalous beats were prefiltered only by the method utilized in the prior art.

FIG. 2b is a graph illustrating the quantification of the multifractal cascade process with our multifractal cascade coefficient (MFCC) for the EKG RR-interval series of FIG. 2a.

FIG. 2c is a graph illustrating the adverse effect of abnormal heartbeats on the local MF Holder coefficient for an EKG RR signal with the prefiltering only of prior art.

FIG. 3a is a graph illustrating the EKG RR signal from FIG. 2a with 16-beat MODWT discrete wavelet smoothing applied according to a preferred embodiment of the present invention. The multifractal scaling region analyzed is specifically chosen to avoid the smoothed region.

FIG. 3b is a graph illustrating the multifractal cascade coefficient (MFCC) for the EKG RR-interval series of FIG. 3a.

FIG. 3c is a graph illustrating the markedly improved results in the calculation of the daytime MF Holder coefficient for the EKG RR-interval series of FIG. 2a as a result of using 16-beat smoothing.

FIG. 7a1 is a "Levy flight" analysis of a CHF patient with 14.4% abnormal beats, with the Levy flight probability distribution function plotted versus number of beats to next abnormal beat event, also showing the expectation for unclustered abnormal beats.

FIG. 7a2 is data for the same patient shown in FIG. 7a1, but in semilog plot to display possible exponential scaling dependence, showing the randomized, non-clustered scaling.

FIG. 7b1 is a Levy flight analysis of a CHF patient with 1% abnormal beats, showing discrete beat clustering over a range of 10–15 beats, and also showing the nonclustered PDF.

FIG. 7b2 shows the same patient as in FIG. 7b1, but in semilog plot to display exponential scaling.

FIG. 7c1 shows a CHF patient with 3.7% abnormal beats, demonstrating a clear beat clustering pattern in a broad region of approximately 20 beats.

FIG. 7c2 shows the patient in FIG. 7c1, but in semilog plot to display exponential scaling.

FIG. 14 shows the daytime CHF/NI ROC for our MF Holder analysis with 8-beat wavelet presmoothing.

DETAILED DESCRIPTION OF THE PREFERRED EMBODIMENT

Figure 1A:
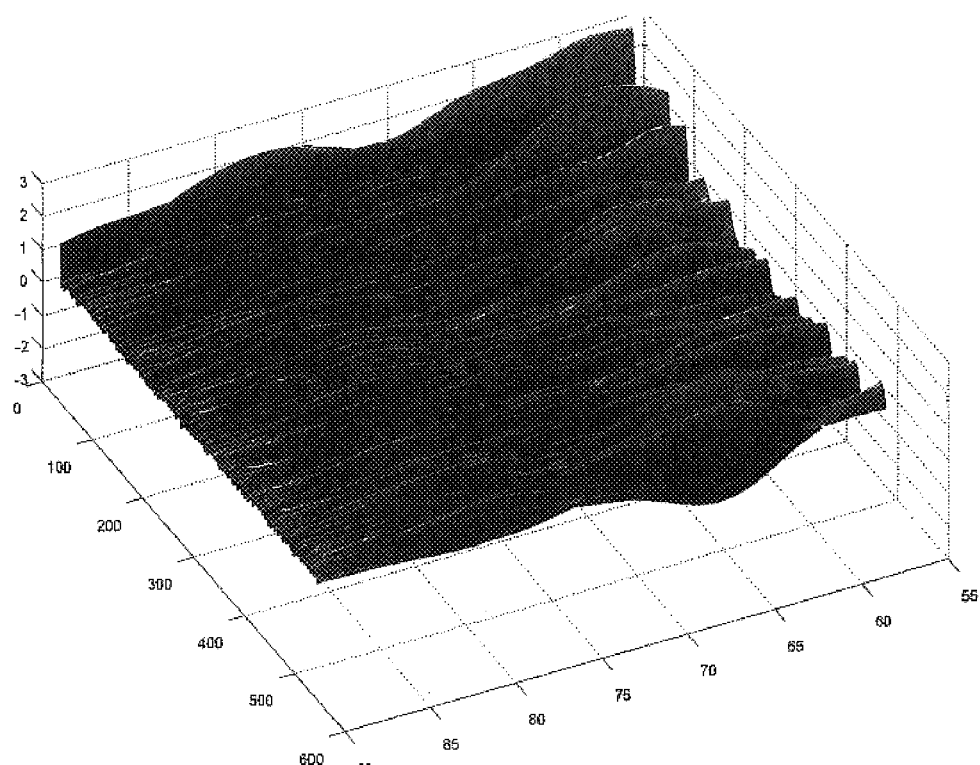
FIG. 1a is the continuous wavelet transform (CWT) of a 512-beat EKG RR-interval series in three dimensions for a healthy individual. The shortest beat intervals are in the lower left hand corner of the x axis (slightly rotated). The y axis is the beat number, and the vertical z axis is the CWT wave amplitude.

1. Multifractal Holder Analysis and Calculation of the Multifractal Cascade Coefficient Fractal analysis is a concept extending traditional statistical analysis to the study of self-similar phenomena. For example, the branching of a tree, the human gut lining, and the human bronchial pathway are fractal or "self-similar." The base of the tree or bronchial stem, for example, shows the same self-similar basic branching pattern that all subsequent branches show, until one reaches the endpoint, namely, leaves, gut microvilli or pulmonary alveoli in these examples. This independence of scale (that is, fractal scaling) is the essence of fractal analysis.

Wavelet analysis as described above acts like a mathematical microscope, and can cleanly separate scale from scale, so each scale can be compared to its adjacent ones for the existence of fractal scaling. This is a major advance over DFA, which only filters out the lower frequency components at each scale. The continuous wavelet transform CWT, a specific type of wavelet transform, is ideally suited for multifractal analysis because the CWT is translation invariant, thus simplifying the mathematical analysis.

Multifractal analysis is a special type of fractal analysis where it is assumed that more than one fractal scaling coefficient defines the characteristics of a given time series segment. If the time series is not multifractal, the analysis simplifies automatically back to the monofractal result. Historically, multifractal analysis (which preceded the advent of wavelet analysis) was complicated by serious technical difficulties. However, recent mathematical advances in wavelet analysis have lead to a new type of multifractal analysis (MFA), called wavelet MFA (wMFA). In general, wMFA utilizes the continuous wavelet transform (CWT) to decompose the one-dimensional time series into a three-dimensional series measuring RR interval amplitude vs. time (beat number) vs. scale (frequency). Decomposition of this complex, wavelet-based, three-dimensional surface into ridge peaks and valleys leads directly to the multifractal formalism. This method significantly extends conventional fractal analysis beyond the measurement of a single Holder fractal scaling coefficient. Details of wMFA for general applications can be found in J. F. Muzzy et al., "The Multifractal Formalism Revisited with Wavelets," International Journal of Bifurcation and Chaos, Vol. 4, No. 2, (1994), 245–302, which is incorporated by reference herein.

The literature on fractal analysis contains a confusing variety of fractal scaling coefficients, called DFA, alpha DFA, Hurst coefficients, etc. Adding to the confusion, the definitions of the fractal scaling coefficients are variable. We use the definition of the Holder coefficient in our analyses, as it depends mathematically on the local exponential nature of the time series, and is precisely defined as being Holder=−0.5 with random white noise. The Hurst coefficient can be shown to be related to the Holder coefficient, and identical in the monofractal situation where H is independent of the moment parameter q (equivalently, the fractal cascade process is described by a single fractal scaling coefficient). We have calibrated all of our analyses with white noise and the Riedi MFM multifractal model, using fractional integration to cover the full fractal range expected for real EKG data. This model is described in R. H. Reidi et al., "A Multifractal Wavelet Model with Application to Network Traffic," IEEE Transactions on Information Theory (Special Issue on Multiscale Signal Analysis), pp. 992–1018 (April 1999), which is hereby incorporated by reference.

(a) The Continuous Wavelet Transform (CWT) of the EKG RR-Interval Series

In this new wMFA formalism, a time series segment to be analyzed is converted into a continuous wavelet transform (CWT). Derivatives of the Gaussian function are generally used as the CWT. We use derivatives of the Gaussian function in our preferred embodiment, since these functions are readily computed, and can be chosen to give optimal temporal and scaling resolution for the analysis. The result of the CWT algorithm is that the one-dimensional EKG RR-interval series analyzed becomes three-dimensional. One dimension is a new scaling dimension, where the amplitude of the time series is now given by a scale resolution of 1 beat, 2 beats, 4 beats, and so on, while retaining the time dependence of the original signal at each scale.

Figure 1B:
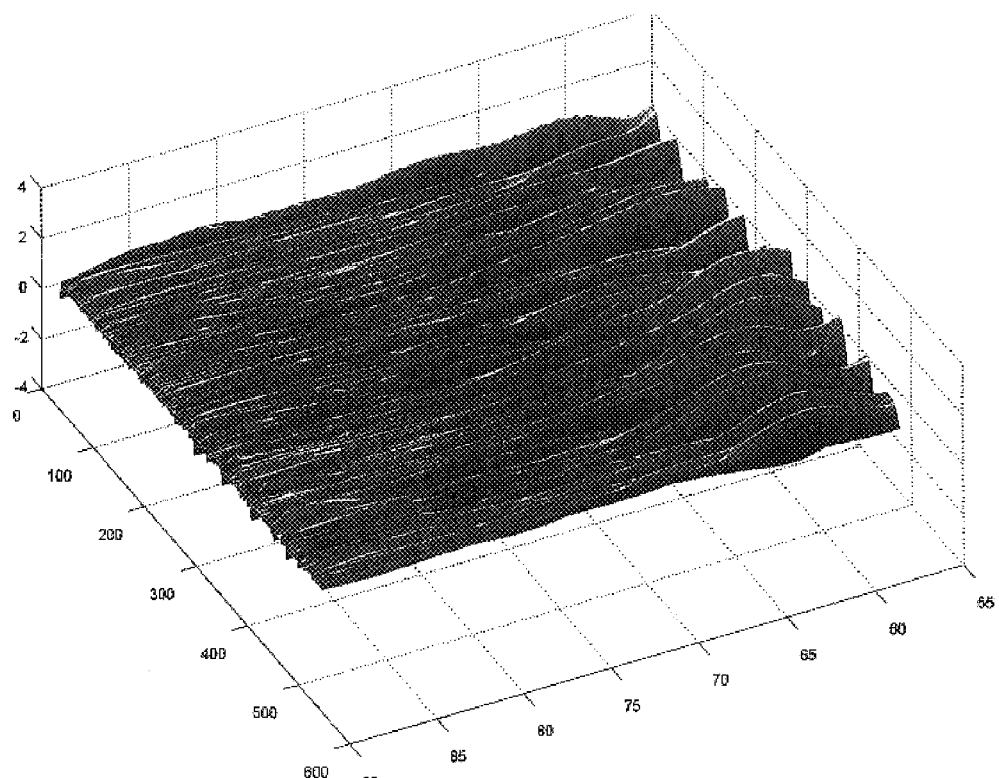
FIG. 1b is the CWT of a 512-beat EKG RR-interval series in three dimensions for a CHF patient with no abnormal beats.
Figure 1C:
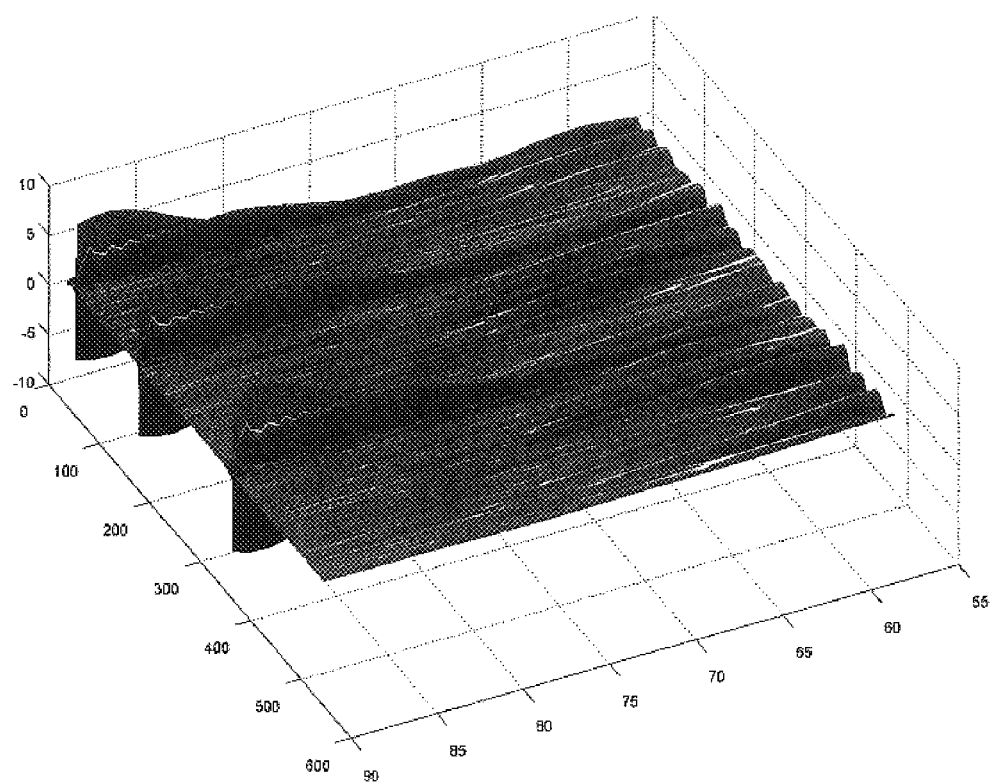
FIG. 1c is the CWT of a 512-beat EKG RR-interval series in three dimensions for a CHF patient with 3% abnormal beats. Three abnormal beats are shown.

FIGS. 1a–c show typical CWT images of a healthy 512-beat EKG snapshot, a corresponding CHF snapshot, and a corresponding CHF EKG snapshot with abnormal beats, respectively. The vertical axis in these figures is the CWT of the EKG RR interval amplitude. The lower RH axis is the scale (a rotated x axis), with 90 being the shortest interval of single-beat resolution, with longer beat intervals (lower resolutions) described for scale values less than 90. The left hand axis (rotated y axis) is the beat number of the time series snapshot, with 512 beats shown.

In comparing FIGS. 1a and 1b, a reduced CWT RR interval amplitude over a wide range of short beat interval scales may be noted in FIG. 1b. This leads to an increased Holder mono- or multifractal scaling coefficient for the data of FIG. 1b, typically of 0.2 or greater, consistent with the fractal EKG literature.

Figure 5:
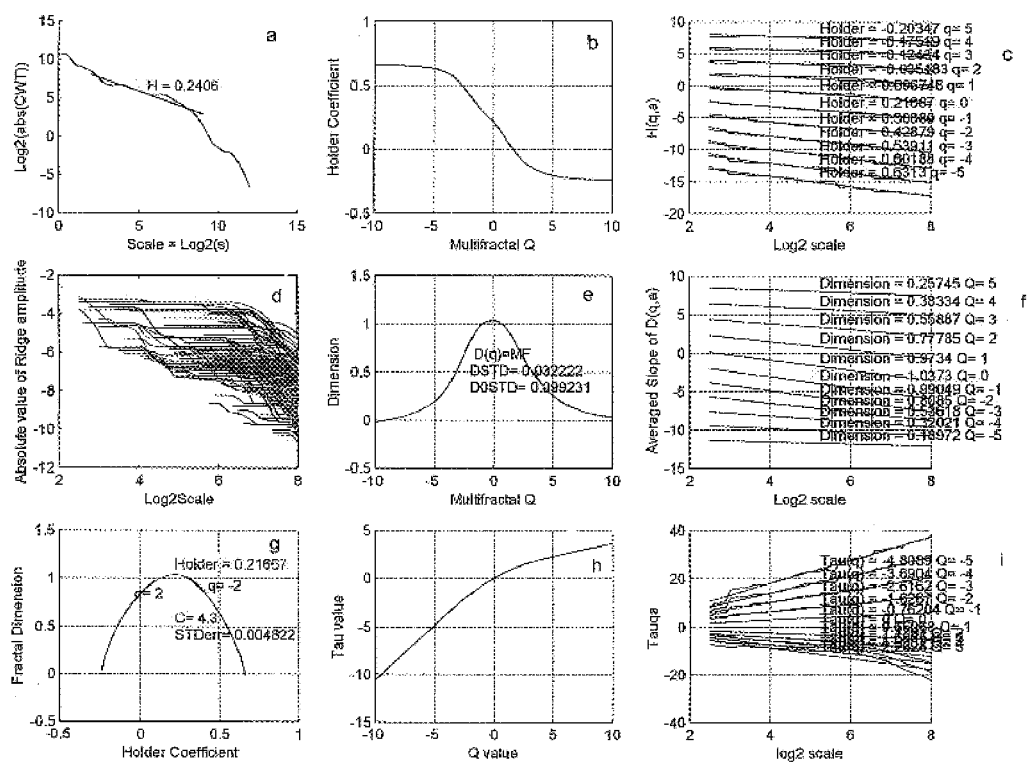
FIG. 5a shows the "monofractal" Holder coefficient calculated for the 4096-beat multifractal Holder snapshot of an EKG time series where the snapshot exhibits multifractal behavior.
FIG. 5b is a graph plotting the MF Holder coefficient H(q) for the multifractal 4096-beat snapshot of FIG. 5a for the range of "q" values from −10 to 10.
FIG. 5c is a graph that depicts the determination of the MF Holder (q, a) coefficients from the wavelet ridges for the 4096-beat multifractal snapshot over the beat scaling range of value "a" (log2 scale) and values of moment parameter "q" from −5 to 5.
FIG. 5d is a graph illustrating the wavelet ridges determined from the CWT of the 4096-beat snapshot.
FIG. 5e is a graph plotting the MF dimension D(q) for the 4096-beat snapshot over the log2 scaling range of 2.5 to 8, and values of q=−10 to 10.
FIG. 5f is a graph illustrating the determination of the MF dimension D(q,a) from the wavelet ridges for the 4096-beat multifractal snapshot over the beat scaling range "a" chosen, and values of "q" from −5 to 5.
FIG. 5g is a graph of the MF Holder coefficient plotted against the MF dimension D(H(q)) for the multifractal 4096-beat snapshot series of FIG. 5.
FIG. 5h is a graph of Tau (q) for the multifractal 4096-beat snapshot.
FIG. 5i is a graph illustrating the determination of the Tau (q, a) value for the multifractal 4096-beat snapshot over beat scaling range "a" and values of "q" from −5 to 5.

FIGS. 5a and 6a are plots of the results of applying the CWT transform to MODWT wavelet smoothed data taken from a typical 4096-beat EKG RR-interval snapshot. The data of FIGS. 5a–i is typical of a healthy individual, and the data of FIGS. 6a–i is typical of a CHF or CAD patient. The data of FIGS. 5a–i is known to be multifractal. The linear scaling range for the snapshot of FIGS. 5a–i and 6a–i was 8 to 405 beats. The CWT transform is applied as described above. The results are plotted in FIGS. 5a and 6a as the base 2 logarithm of the beat interval scale (largest scales on left, smallest on right in each figure) against the base 2 logarithm of the absolute value of the CWT amplitude.

The monofractal Holder coefficient for the data of FIGS. 5a–i and 6a–i is generated simply by using the slope of the resulting curve in FIGS. 5a and 6a and subtracting ½. This can be verified with standard calibrator monofractal or multifractal test time series generators; for example, white noise should give a Holder coefficient of −0.5. The scaling range chosen should also be such that the slope is reasonably constant over this range. The straight black line in FIGS. 5a and 6a show the scaling range chosen for the calculation of the monofractal Holder coefficient. The monofractal Holder coefficient in FIG. 5a over the chosen scaling range is 0.2406, whereas the multifractal Holder coefficient for the same snapshot, as shown in FIG. 5g, is 0.21667. The multifractal Holder scaling range is chosen differently from the monofractal Holder scaling range, by empirical examination of the H(q,a) and Tau (q, a) log plots shown in FIGS. 5c and 5i, respectively.

FIGS. 5c and 6c are log-log plots of the multifractal Holder coefficients H(q, a) for values of q from −5 to 5. Small values of "a" (small log2 scale) correspond to very short beat intervals. In this 4096-beat snapshot, log2=11 corresponds to 1-beat resolution, and log2=2 corresponds to 512-beat resolution. The scaling range chosen was from log2=2.5 to log2=8 in dyadic scales, or a linear scaling range of 8 to 405 beats. The Holder coefficients are calculated directly from the values of Z(q, a). (The calculation of Z(q, a) is described below.) When the analysis is limited to a particular beat-scaling range chosen empirically for the data in question as described above, the coefficients H(q, a) generate H(q) shown in FIGS. 5b and 6b. Note that for H(q=0), the multifractal Holder coefficient reduces to the equivalent of the monofractal Holder coefficient, but does not always agree precisely with the monofractal Holder coefficient. The explanation for this is that q=0 corresponds to the zeroth moment of the multifractal PDF, which can be shown mathematically to reduce to the monofractal Holder in the absence of the multifractal cascade. Another way of seeing this is that analysis of a monofractal time series with the multifractal analysis generates a sharply peaked D(H(q)) such as FIG. 6g (this process will be described in greater detail below). The Holder coefficient at the peak of D(H(q)) is also H(q=0). Conventional monofractal Holder analysis can be shown to generate the same answer if both monofractal and multifractal analyses are calibrated correctly.

FIGS. 5i and 6i plot the value of Tau (q, a) as a function of the scale value a. The value of Tau (q, a) can also be derived from the calculation of Z (q, a) or by a direct calculation. Just as for the MF Holder coefficients H(q) and the multifractal dimension D(q), once the MF scaling range is chosen, Tau (q, a) may be reduced to Tau (q). It should be noted that Tau (q) is much straighter in FIG. 6h than in FIG. 5h, revealing the increased multifractality of the snapshot used in FIGS. 5a–i. Monofractality can be defined by the lack of dependence of Tau(q) upon moment parameter q. This concept is explored in the work of Ivanov et al. cited above. We expand upon the work of Ivanov et al. by recognizing and utilizing the fact that mono- or multifractality is a relative concept, and should best be defined with a quantitative number, such as our MFCC, for this analysis.

Returning to our discussion of the method of determining the multifractal Holder scaling range, it should be noted that this method is analogous to the linearity check of the monofractal Holder coefficient, where now the linearity check must be for each value of the moment coefficient q. Often the validity of the multifractal scaling range is best determined from the Tau(q, a) curves. As already noted, the Tau(q, a) curves should approximate a straight line for each value of q over the desired scaling range on the log-log plots. The validity of the choice of the multifractal scaling range can also be seen in the graph of D(q) in FIG. 5f. FIGS. 5f and 6f plot the dimension D(q, a) as a function of the scale a, which is directly related to the beat resolution. Like H(q, a), D(q, a) is also derived from Z(q, a). After the scaling range is chosen empirically as described, D(q, a) generates D(q). D(q=0) is the capacity dimension of the time series, which should be equal to one. In this figure, D(q=0)=1.0373, which is a very good approximation to the capacity dimension expected for a one-dimensional line.

FIGS. 5b and 6b are plots of the value of the multifractal Holder coefficient H(q) as a function of q for values of q from −10 to 10. As noted above, H(q=0) is the equivalent of the monofractal Holder coefficient. If the value of H(q) drops monotonically from left to right, this is an indication that the multifractal cascade is generally well-defined. As can be seen in FIG. 5b, the value of H(q) drops smoothly from q=−10 to q=10. This indicates that the multifractal cascade for this data is in fact well-defined. By contrast, the value of H(q) in FIG. 6b drops smoothly only from q=−10 to q=−2, rises slightly from q=−2 to q=0, and then drops steadily again. A region thus exists where H is relatively independent of q, a condition not typical of multifractality, and therefore suggesting monofractality.

FIGS. 5e and 6e are plots of the multifractal dimension coefficient D(q) as a function of q for values of q from −10 to 10. D(q=0) as explained above is known as the capacity dimension, and should represent the maximum value of one for a one-dimensional fractal object, such as an EKG time series. If D(q=0) is less than one, then this may be an indication that the chosen scaling range is insufficient, or that the snapshot chosen is too small. If D(q) is not in the form of a concave downward curve, peaking at q=0, the snapshot chosen may be overlapping a change in the multifractal properties of the time series, and thus the multifractal cascade may not be defined. As can be seen in FIG. 6e, the plot for D(q) is flattened on top and does not quite reach a value of 1. This may be an indication of problems with the multifractality of this data. By contrast, in FIG. 5e, the curve is smooth and closely approaches a value of D(q)=1 at q=0.

It should be noted that for q=0, the multifractal analysis corresponds qualitatively with the monofractal method for calculating the Holder coefficient by a much simpler method, namely a crude average over the time series snapshot chosen. In contrast, the multifractal Holder coefficient H(q) is a number that reflects all of the temporal "nooks and crannies" of the time series, with different values of q weighting the emphasis on different scales. There are significant other known benefits of MFA over the conventional monofractal method in that much more information is obtained from the time series. For example, a value of D(q=2) gives the "correlation" dimension, which is useful in many practical fractal problems since the fractal dimension for this value can be generated by simple counting procedures. The capacity dimension given by D(q=0) is the most commonly known dimension: 1 for a line, 2 for a surface, 3 for a solid object. The Shannon information dimension is given by D(q=1), also known as the Shannon entropy. Values of q>2 or q<0 also generate new information about the time series, but less is known about them. We do know, however, that very negative q values extract information about very small, fast fluctuations, and very positive q values extract information about slow, large fluctuations in the time series analyzed. The multifractal dimension D(H(q)) reveals the dimensional complexity of the time series snapshot in regions defined by very positive values of q, and regions defined by very negative values of q.

Figure 6:
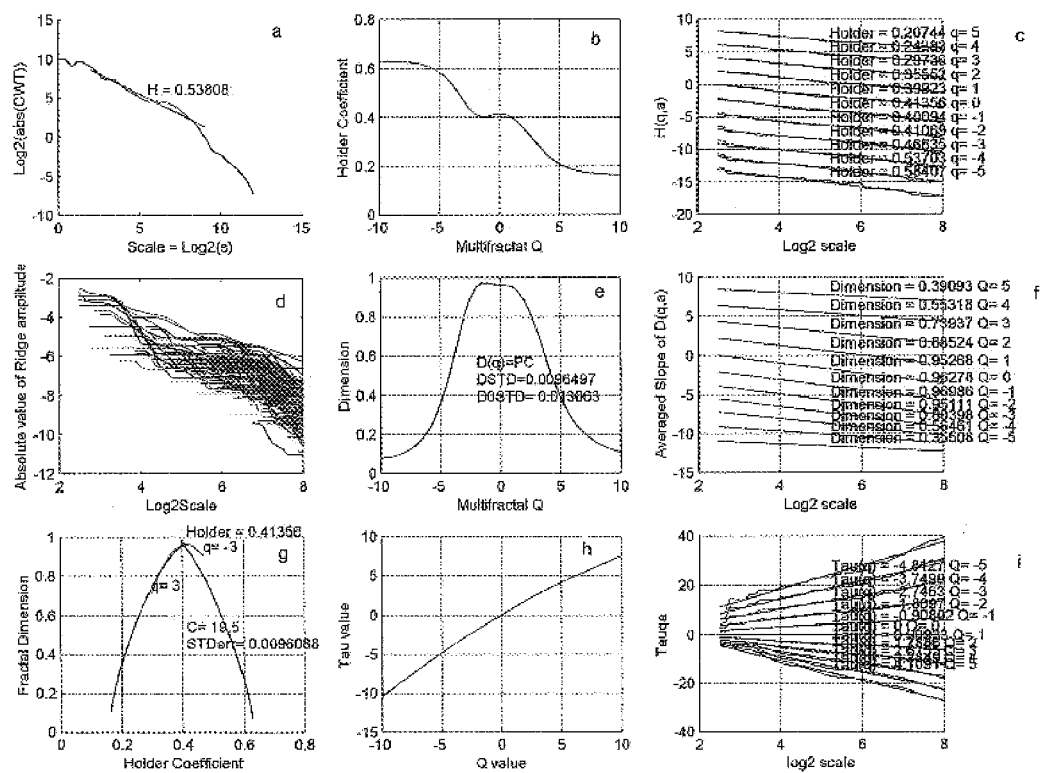
FIG. 6a is a graph demonstrating the determination of the "monofractal" Holder coefficient for a 4096-beat snapshot of an EKG time series exhibiting monofractal behavior.
FIG. 6b is a graph plotting the MF Holder coefficient H(q) for the monofractal 4096-beat snapshot over values of q=−10 to 10.
FIG. 6c illustrates the determination of the MF H(q, a) coefficients from the wavelet ridges for the monofractal 4096-beat snapshot over the selected scaling range and q values from −5 to 5.
FIG. 6d is a graph illustrating the CWT wavelet ridges for the monofractal 4096-beat snapshot.
FIG. 6e depicts the MF dimension D(q) for the monofractal 4096-beat snapshot for values of q from −10 to 10.
FIG. 6f is a graph illustrating the determination of the MF dimension D(q, a) for the monofractal 4096-beat snapshot of the series of FIGS. 6a–i for the selected scaling range shown and for values of q from −5 to 5.
FIG. 6g is a graph of the MF Holder coefficient plotted against the MF dimension D(H(q)) for the monofractal 4096-beat snapshot of FIGS. 6a–i.
FIG. 6h is a graph of the Tau values plotted against q for the monofractal 4096-beat snapshot.
FIG. 6i illustrates the determination of Tau (q, a) for the monofractal 4096-beat snapshot for the selected scaling range shown and for q=−5 to 5.

Examination of FIG. 6e shows that D(q) is constant from q=−2 to q=1, and FIG. 6g shows that D(H) has a sharp peak at H=0.41356. This is H(q=0). (The monofractal value of H for this snapshot was 0.53808.) Comparison of FIGS. 6e and 6g to FIGS. 5e and 5g shows a much broader D(H), and a more sharply peaked D(q), indicating that the snapshot used for FIGS. 6a–i is much less multifractal than the snapshot used for FIGS. 5a–i. Our MFCC also shows this as the MFCC of FIG. 6 is 1/(19.5), and 1/(4.3) in FIG. 5, as explained more fully below.

(b) Wavelet Ridge Analysis

The three-dimensional CWT snapshots of the RR-interval series segment as shown in FIGS. 1a–c can be decomposed into much simpler datasets consisting only of continuous ridge and valley lines by creating a ridge skeleton. The process of determining the ridge map can be considered conceptually equivalent to drawing lines over the wavelet ridges and valleys, so that the path of an imaginary river can be predicted passing along the valley lines. The general technique for generating such ridge maps is described in the wMFA references incorporated herein. It can be shown mathematically that the key temporal and scaling information contained in the original signal is retained in this ridge map skeleton, as demonstrated in S. Mallat et al., "Singularity Detection and Processing with Wavelets," IEEE Transactions on Information Theory Vol. 38, No. 2, March 1992, pp. 617–643; and W. -L. Hwang et al., "Characterization of Self-Similar Multifractals with Wavelet Maxima," NYU Technical Report No. 641 (Computer Science Dept. July 1993), both of which are incorporated herein by reference.

FIGS. 5d and 6d are plots of the wavelet ridges resulting from the continuous wavelet transform. The wavelet ridges are determined by reducing the three-dimensional continuous wavelet transform of the snapshot to lines that represent the ridges and valleys of the continuous wavelet transform, scale by scale. This wavelet ridge generation from the continuous wavelet transform can best be described as being like a contour-map analysis of a mountain range. For example, imagine drawing a line through the maxima of all mountaintop ridges, and the minima of all valleys. If done correctly, the minima will follow the path a river would take though each valley from short RR-interval scales to long ones. It can be shown from the multifractal formalism that the basic mathematical features necessary to reconstruct the time series are still contained in the ridges, which offers a considerable simplification of the analysis. The so-called thermodynamic distribution function Z(q, a) described above can then be determined directly from the wavelet ridges, and the multifractal cascade information derived from Z(q, a). As explained above, the parameter q is a moment parameter that is very important in describing the multifractal analysis.

(c) Calculation of the Thermodynamic Multifractal Partition Coefficient Z(q,a)

The ridge skeleton map, identifying key peaks determined scale by scale, is used to determine the "thermodynamic" partition coefficient Z(q, a), where a is the beat scaling parameter, and q is an exponential moment parameter. The general mathematical method of determining Z(q, a) is described in references previously cited. The role of this parameter has already been described as a basis for calculation of certain important parameters in our analysis. For Z(q, a) to be defined for negative q, it must be modified slightly by summing over wavelet ridge peaks using a "sup" scaling method described in A. Arneodo et al., "A Wavelet-Based Method for Multifractal Image Analysis. I. Methodology and Test Applications on Isotropic and Anisotropic Random Rough Surfaces," The European Physical Journal B 15, 567–600 (2000), which is incorporated herein by reference.

(d) The Legendre Transform to Calculate the MF Cascade D(H)

The multifractal "thermodynamic" partition coefficient Z(q, a) can be used to generate additional useful information about the time series. The relationship between the MF Holder coefficient and the "dimension" D(H) can be determined with a Legendre transform (change of variables), and an empirically determined suitable choice of a beat scaling range to be analyzed. This mathematical calculation is described in Boston University work already incorporated by reference. The result is an downwardly facing convex curve with the maximum of D(H) at q=0. The width of D(H) reflects the range of the (possibly multifractal) Holder coefficients present in the chosen time-series snapshot, demonstrating the properties of the observed multifractal cascade process. The width of this curve gives a measure of the multifractality of the Holder coefficients for the time series snapshot and scaling range analyzed. A smooth broad curve indicates multifractality, that is, that H has different values for different scales analyzed. This is illustrated in FIG. 5g, which shows a multifractal cascade process. Our MFCC approximation is shown by the red line in the figure. In contrast, the snapshot analyzed in FIG. 6g has a pointed peak at H(q=0) indicating monofractality. In cases where the multifractal cascade is defined, the D(H(q)) curve should be continuous, smoothly rising from a minimum for low values of H (large positive q), reach a maximum value of D at the most likely value of H=H(q=0) for the snapshot, and then fall for large values of negative q.

As explained more fully below, the MFA method offers a solid mathematical foundation for examining the "attractor" of the process being studied, namely the Lyupanov exponent from the Komolgorov-Smirnov entropy, and the newer Tsallis entropic index q. Other entropies, such as the Pesin entropies, can be derived. We believe these other parameters derived from the basic MF Holder analysis will have clinical value in EKG analysis, as the relatively crude approximate entropy (ApEn) has already been determined to have diagnostic value in several clinical EKG studies. The general mathematical methods used to calculate these entropies are explained in L. Y. Lin et al., supra; S. M. Pinkus et al., "Approximate Entropy: Statistical Properties and Applications," Communications Statistical Theory Methods 21:3061–3077 (1992); S. M. Pinkus et al., "Approximate Entropy as a Measure of System Complexity," Proceedings of the National Academy of Sciences USA, 88:2297–2301 (1991); H. V. Huikuri et al., "Dynamic Behavior and Autonomic Regulation of Ectopic Atrial Pacemakers," Circulation 1999;100:1416–1422; and M. P. Tulppo et al., "Effects of Exercise and Passive Head-Up Tilt on Fractal and Complexity Properties of Heart Rate Dynamics," American Journal of Physiology Heart Circulation Physiology 280:H1081–H1087, 2001, each of which are incorporated herein by reference.

(e) The Multifractal Cascade Coefficient, MFCC

In a preferred embodiment of the present invention, we quantify the degree of multifractality with a single coefficient C that we call the multifractal cascade coefficient (MFCC=1/C), when the multifractal cascade dimensional curve D(H(q)) is defined. This is a significant advance over prior art, where the multifractal cascade was analyzed in a qualitative manner only. It is our belief that the definition of monofractality or multifractality should not be a black or white concept, but should represent a continuum. Our MF Holder analysis supports this premise, as normal or heart failure patients both have various degrees of snapshot multifractality. It is the time average of these snapshots that determines the degree of EKG multifractality for each individual.

We approximate the dependence of the multifractal dimension D(H(q)) on H(q) with a curve-fitting algorithm, where the preferred embodiment is a single parabolic coefficient. In FIG. 5g, we illustrate a typical calculation of the parabolic MFCC using a least squares fit approximation to fit the long D(H) curve to the shorter curve approximation. The value C in the figure is the resulting parabolic coefficient, with standard error as noted in the figure. Note the excellent agreement between the approximation and actual plot of D(H(q)). In most multifractal cases where the beat scaling range is appropriately chosen, this model is a very good approximation, thus permitting quantification of the multifractal cascade.

Monofractality (or more precisely weak multifractality) is demonstrated when D(H(q)) is sharply peaked as a function of H(q), and has a very large quadratic MFCC. A good example of a monofractal cascade is shown in FIG. 6g, where the quadratic MFCC curve is less accurate, and only approximates the sharp peak of D(H(q)); the MFCC analysis still does a good job, however, of separating degrees of multifractality. We exclude cases where our multifractal model cannot generate a smooth curve for D(H(q)), in which case the multifractal cascade is not defined. These events are similar to thermodynamic "phase changes" (PC) in other applications. This PC regime is not well understood, and probably represents a combination of more than one multifractal cascade process in the same snapshot.

Empirical experimental analysis with 37 CHF patients and 12 healthy control patients indicates that a value of C equal to or exceeding about 11 indicates that the data is monofractal. As shown in the figures, the C of FIG. 5g has a value of 4.3, indicating that the data is multifractal. It is evident that the broader D(H(q)) becomes, the more monofractal the snapshot analyzed, and the greater the value of C becomes. Comparing FIGS. 5g and 6g, one may note the narrow, pointed convex upward shape characteristic of monofractality in FIG. 6g. The short curve in this figure is again the MFCC approximation, revealing a C value of 19.5, well into the monofractal range. Some snapshots can be even more monofractal, with C values approaching 100. Note also that the curve fit is not as good as with the multifractal data, where the fit can be nearly perfect. Despite the imperfect curve fit, the qualitative scaling of monofractality against multifractality is still well represented with one scaling parameter C.

2. Step-by Step Analysis of EKG RR-Interval Series Data

The application of these MFA principles to a time series of experimental EKG data according to a preferred embodiment of the invention, and the method used in order to differentiate between healthy and CHF patients according to a preferred embodiment of the invention, will now be described.

(a) Prefiltering to Remove Rare Aberrant, Noise Beats

In a preferred embodiment of the invention, the time series to be analyzed is prefiltered with a discrete wavelet method to identify single beats more than 2–3 standard deviations from an 8-beat moving average. We remove a maximum of 2% beats with this method. Typically, we find that only about 0.5% to 0.8% single beat removal is sufficient.

We have discovered that many CHF and CAD patients have real abnormal beat events that can seriously degrade the calculation of the Holder coefficient even after such prefiltering. FIG. 1c shows 3 typical abnormal beats, demonstrating their regularity, and thus the low likelihood that they are noise. The EKG literature has not focused on such patients, and has only examined patients without arrhythmias, as the conventional 2% maximum filtering method is not sufficient to remove these beats which can represent as much as 15% of the EKG RR-interval series. Such patients also have daytime MF Holder coefficients of −0.3 to −0.4, much lower than expectations for a normal Holder coefficient. Furthermore, FIGS. 2a–c demonstrate that even abnormal beats as rare as 1% can adversely affect the MF Holder coefficient.

The adverse effects of abnormal beats even after the typical 0.5% to 2% maximum prefiltering can be seen in FIG. 2a, where 1% abnormal beats were detected with Levy flight analysis. This graph contains regions where the local heart rate appears to vary abruptly from 60–120 beats (60 beats wide) in the first two hours of the recording. One can also see through a comparison of FIGS. 2a and 2c that the MF Holder coefficient drops during the time when the abnormal beats are unusually prominent. Note in particular the dramatic drop in H at 1–2 hours. Earlier work incorrectly suggests that the Holder coefficients for CHF patients without arrhythmias should be significantly higher than the values shown.

We conclude therefore that the prior art method of removing up to 2% of the beats, and choosing a fractal scaling region for analysis that excludes the 16- or less beat interval region, is not sufficient. Our greatly improved MF Holder analysis using the special 8–16 beat wavelet smoothing step before the MFA largely solves this problem as described in detail below. It should be noted that this process does not involve the removal of any scaling region that is to be examined for multifractal scaling analysis.

(b) The Existence of Abnormal Beats and Beat Clustering

We have determined that 20% of our 47 heart disease patients have significant numbers (>5%) of abnormal beats, in some cases as many as 15% abnormal beats. To make matters worse, even relatively rare abnormal beats can be clustered in time, making them hard to remove with the conventional prefiltering analysis used in prior art; examples of clustered abnormal beats are illustrated in FIGS. 2a–2c. A preferred embodiment of our invention thus comprises three additional steps added to the MF Holder analysis, namely, the detection of abnormal beats, the detection of abnormal beat clustering, and the wavelet smoothing step. All of these steps are preferably to be performed before beginning the MF analysis.

(c) Formal Levy Flight Detection of Abnormal Beats, and Beat Clustering

Figure 16:
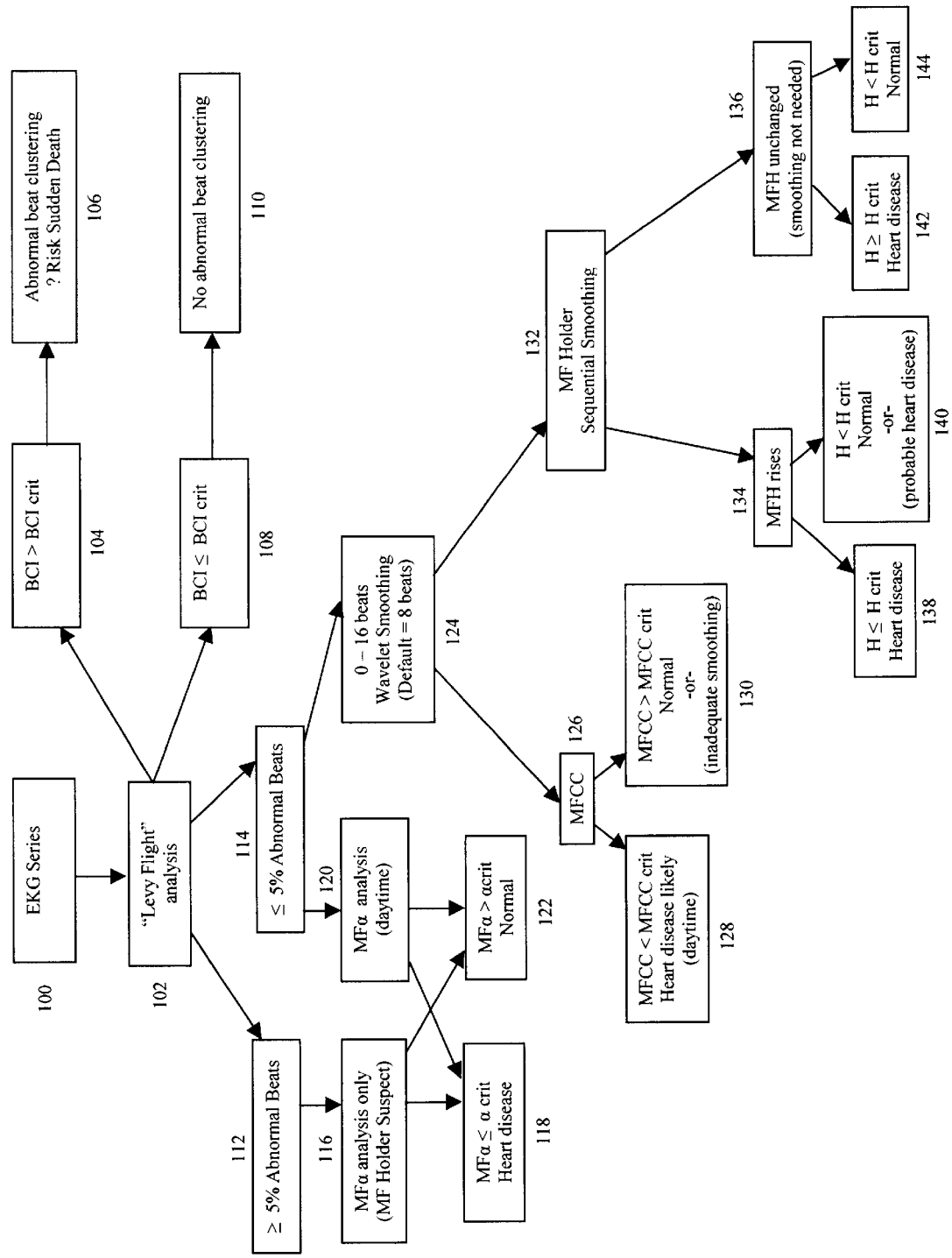
FIG. 16 is a flow chart depicting in a preferred embodiment our multivariant diagnostic application of (1) "Levy flight" analysis for calculating the percentage of abnormal beats and our Beat Cluster Index (BCI); (2) MF alpha analysis; (3) MF Holder analysis (with default 8-beat smoothing), and (4) sequential beat smoothing analysis with subsequent MF Holder analysis, for the evaluation of a typical EKG RR-interval series.

Referring now to FIG. 16, our first step in a preferred embodiment of our MFA of a 24-hour EKG time series 100 is to perform what we shall term a Levy flight abnormal beat detection analysis at block 102. This analysis is based on determining whether the delay from one abnormal beat event to the next is correlated in time or random. Time-series data of this type may show unusual non-Gaussian statistical characteristics best described by a more general Levy-type distribution. Levy distributions may show power law dependence (log-log), rather than exponential scaling (semi-log or log-linear). Levy flight analysis is discussed in general in T. H. Solomon et al., "Chaotic Advection in a Two-Dimensional Flow: Levy flights and Anomalous Diffusion," Physica D 76 70–84 (1994); and C. -K. Peng, "Long Range Anticorrelations and Non-Gaussian Behavior of the Heartbeat," Physical Review Letters, vol. 70, no. 9, 1343–1346 (Mar. 1, 1993), each of which is hereby incorporated by reference.

We have shown that abnormal beats are common in CHF and CAD patients, and have a significant effect on fractal analysis. FIG. 1c illustrates a typical CWT abnormal beat pattern (with 3 abnormal beats) in a heart failure patient with 3% abnormal beats. A 512-beat RR-interval segment is shown. Very short (i.e., single-beat) interval scales lie in the lower left-hand corner at 90, whereas lower numbers to the right of this figure reflect longer scales. Comparison to heart failure patients without abnormal beats reveals that heart failure patients normally have relatively few beat fluctuations at short beat intervals compared to healthy individuals, indicated by the areas between the abnormal beats. Prior multifractal work has generally ignored this 1–16 beat region, but, as we have shown, this does not eliminate the effect of these beats. FIG. 1c also shows that these aberrant beat events can be quite reproducible, making their interpretation as noise unlikely. Our work confirms that this scaling region may consist of a noise pattern in some patients, but our snapshot method can discriminate between the "noise beat" situation and aberrant beats. Also, all of our EKG RR-interval datasets have been pre-screened to ensure that noise beats have been excluded. We only analyze continuous unaltered datasets, with the exception of the 0.6% anomalous beat prefiltering.

We use the single beat scale (highest) resolution CWT as a detector of these abnormal beats by calculating the local variance of the time series, and count only single-beat events with a variance that is more than three standard deviations over a local 4-beat moving window. We calibrated this abnormal beat detector by determining that most of the abnormal beats seen in the CWT were detected, and that the healthy patients had no abnormal beats. We then determined our Levy flight probability distribution by recording sequentially the number of beats to the next abnormal beat, and incrementing the Levy PDF (beat number) for that beat number. We also randomized the abnormal beat interval series for each patient, so that comparison could readily be made with a reference unclustered situation. In our preferred embodiment, we analyze the 4–26 beat region on a semi-log plot, where the randomized analysis gives an exponential scaling coefficient equal to the percentage of abnormal beats. Usually the patient data does not give a power law distribution in this beat range, and shows exponential decay. We have found empirically that the ratio of the patients Levy flight scaling exponent to the randomized scaling exponent over the 4–26 beat range gives a good indicator of the presence or absence of beat clustering in most patients. We call this ratio the beat clustering index (BCI).

Figure 2:
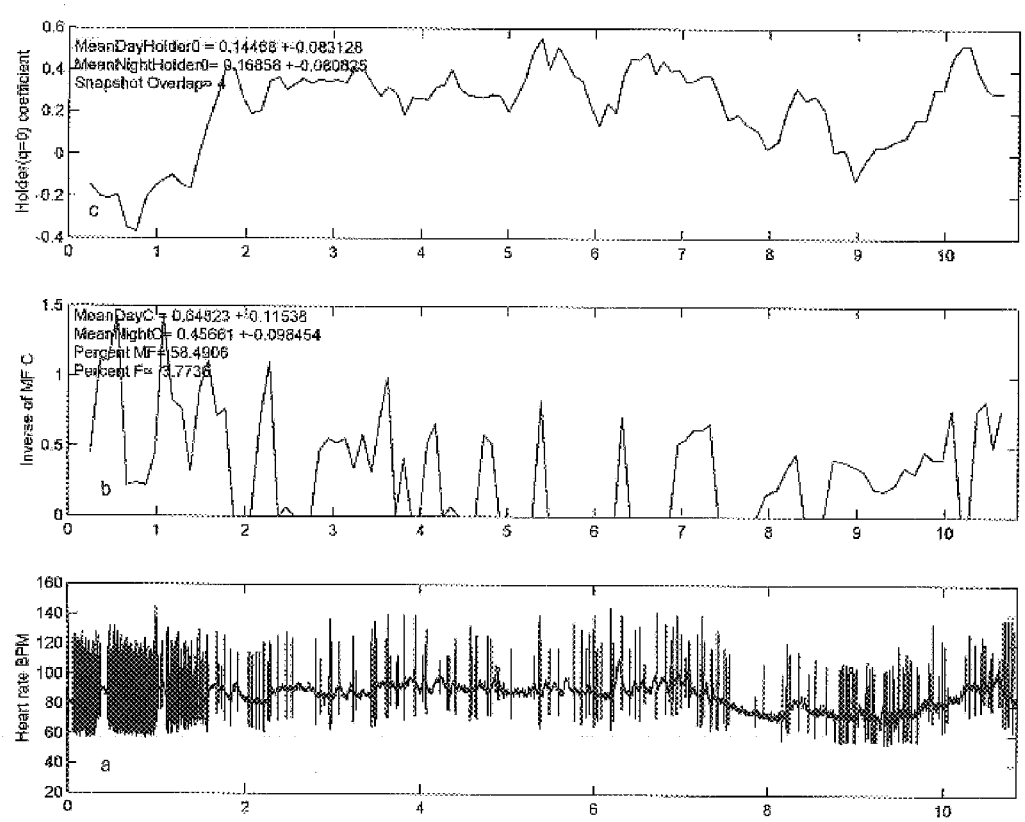

We have performed Levy flight analysis on all of the 32 CHF and 15 CAD patients in our study, which consists of the BCI and the abnormal beat frequency. FIG. 7a1 shows the Levy PDF for a CHF patient with 14.4% abnormal beats, from an EKG RR-interval series analyzed over a 24-hour time period. The red line is the randomized PDF for this patient. The minimum resolution limit for the Levy flight analysis seems to be 3–4 beats. FIG. 7a2 is a semilog plot for the patient data in FIG. 7a1, showing good linearity from 4–26 beats, indicating consistency with an exponential distribution. Comparison to the red randomized data gave a BCI of 1.6, which appears to be consistent with the absence of significant beat clustering, given our patient population. One may compare FIG. 7b1 to FIG. 7a1, where we have analyzed a CHF patient with 1.1% abnormal beats. In this case, there is evidence of beat clustering in remarkably discrete peaks covering the beat interval range of 5–15 beats. The semilog plot in FIG. 7b2 shows that the BCI is now 7.9, indicating strong beat clustering. Another case of abnormal beat clustering is evident in FIG. 7c1, in a CHF patient with 3.7% abnormal beats. One may note that there is a single, broad peak at approximately 6–15 beats. The semilog plot of FIG. 7c2 shows that the BCI is 4.07, indicating beat clustering. Referring to FIG. 16, if the BCI is less than equal to the critical BCI value (determined as noted above) at block 108, then we determine that there is no abnormal beat clustering at block 110. If the BCI is greater than the critical BCI value at block 104, then we determine that the patient is at risk of sudden death due to the abnormal beat clustering at block 106.

Figure 8:
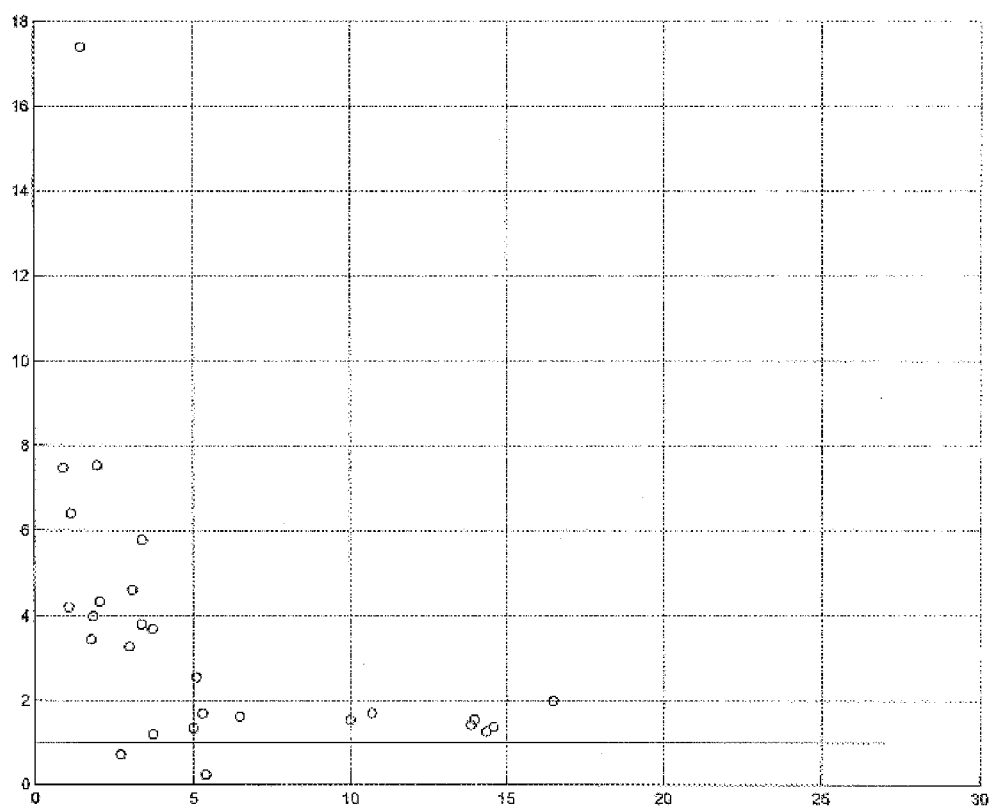
FIG. 8 shows an exponential beat clustering summary for 34 CHF patients and 15 CAD patients analyzed over the 4–26 beat range.

FIG. 8 shows a summary plot of BCI's for all of our 47 patients. This data demonstrates that patients with >5% abnormal beats do not have significant abnormal beat clustering. In addition, it is apparent that patients with <5% abnormal beats can have a BCI that ranges from normal (1–1.5) to 8 or more. We believe that the reason for the absence of abnormal beat clustering in patients with >5% abnormal beats may be due to the fact that patients with significant beat clustering in this group do not survive.

(d) The Wavelet Smoothing Process

As explained above, we have determined that it is necessary to smooth the initial time series with a very high quality discrete wavelet smoothing process that removes only the shortest beat interval scales without affecting longer time scales of the time series. Since the smoothing only removes time scales ignored in the MF Holder analysis, it should not adversely affect the results, and we have verified this result experimentally in our study. This method also greatly improves the diagnostic value of the MF Holder analysis. In the preferred embodiment, we use an 8-beat smoothing method (outside the fractal scaling region to be analyzed), illustrated in FIG. 16 at block 124. We use this same method to analyze all normal and heart disease patients so that analytical artifacts may be ignored.

The smoothing is achieved by applying a Daubechies D8-type discrete (dyadic) wavelet transform smoothing method, called the maximal overlap discrete wavelet transform (MODWT). MODWT smoothing is described in general mathematical terms at D. B. Percival et al., "Wavelet Methods for Time Series Analysis," Cambridge University Press (2001), which is incorporated herein by reference. The result of the smoothing is linked to removal of the smoothed region, usually scales shorter than 8 beats for an 8-beat smoothing. This technique does not alter the phase relationships of any components of the time series longer than the 8-beat minimum scale.

A comparison of the results in FIGS. 2a–c and 3a–c demonstrates the effectiveness of our method. In FIGS. 2a–c, only a 0.6% maximum prefiltering was taken as in prior art, and the first 8 beats were ignored in the multifractal scaling step. Although not shown in FIGS. 2a–c, an increase of this conventional method of analysis to remove up to 2% of the anomalous beats will not improve the results, presumably because the anomalous beats were (visibly) clustered in time in this case (an enhancing effect of approximately one order of magnitude). In addition, as has already been noted above, it is not uncommon for patients to exhibit abnormal/arrhythmic beats to as much as 15% of the total EKG time series. Plainly then, the prior art method of FIGS. 2a–2c cannot be used in a general CHF patient population.

Figure 3:
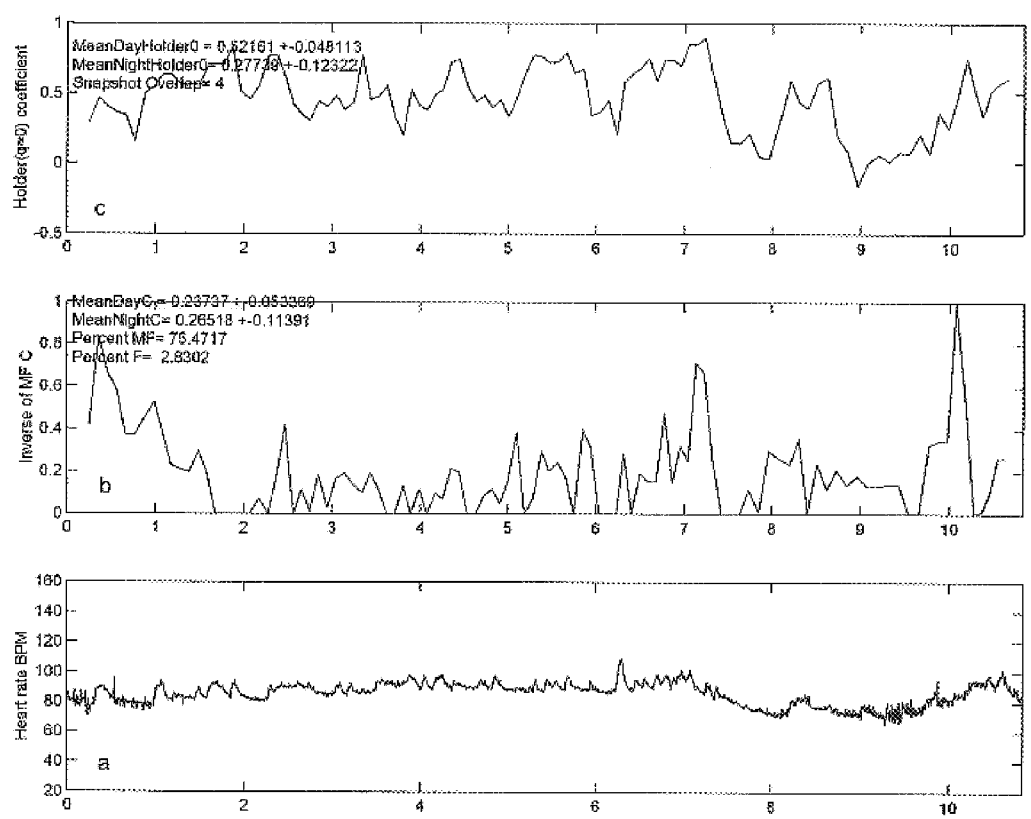

FIG. 3a depicts the EKG data for the same patient as that shown in FIG. 2a, except that in this case 16-beat wavelet smoothing according to a preferred embodiment of the invention was applied. The baseline 8-beat filtering used in this embodiment was visibly not sufficient to remove all of the effects of the clustered abnormal beats. Prefiltering and other measurement parameters are otherwise identical to that performed to achieve the results shown in FIG. 2a. In comparing FIG. 2a to FIG. 3a, however, there is a significantly reduced abnormal beat activity. Furthermore, the dip in the MF Holder coefficient seen in FIG. 2a is now virtually gone.

Figure 4A:
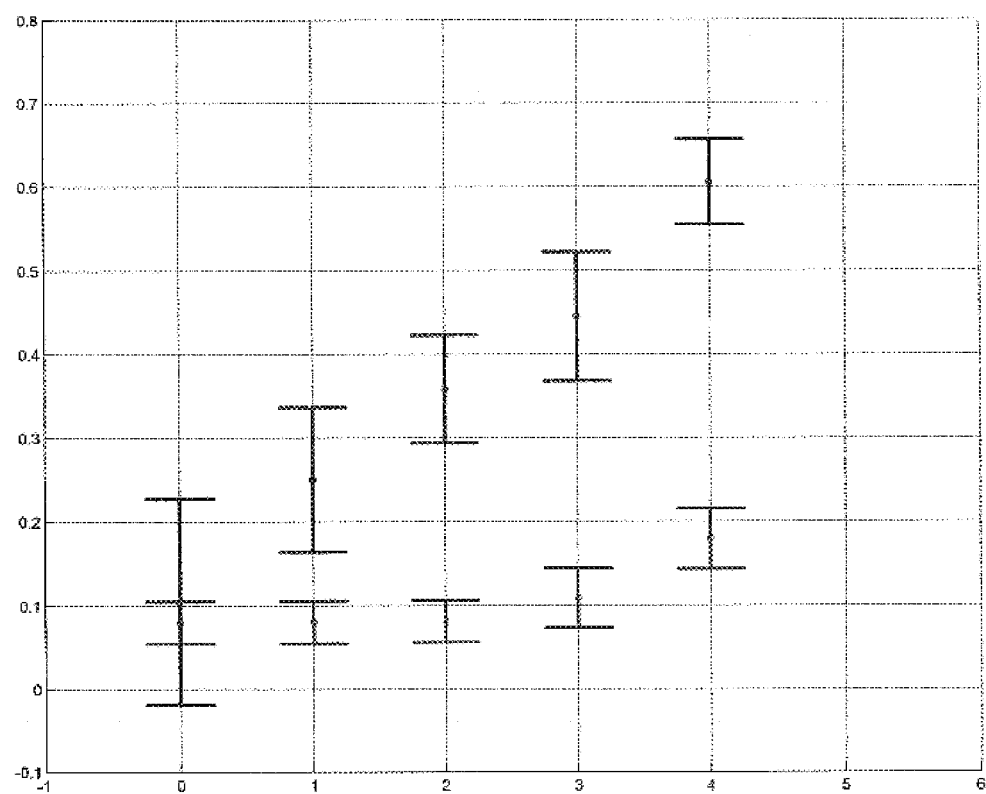
FIG. 4a is a graph illustrating the progressive effect of various stages of discrete wavelet smoothing from none to 16-beat smoothing on the daytime MF Holder coefficient of the CHF patient of FIGS. 2a–c and 3a–c with 1% abnormal/arrhythmic beats, according to a preferred embodiment of the invention.

Turning to FIG. 4a, the ability of the present invention to improve the discrimination between healthy and CHF patients is demonstrated. In FIG. 4a, the Holder coefficient range is plotted against the degree of MODWT discrete wavelet smoothing, with all other analytic parameters remaining fixed. We should point out that the MF scaling region is carefully chosen to exclude the scaling region affected by the wavelet smoothing. Data is given for J=0, 1, 2, 3, and 4. J is a value that correlates to the degree of dyadic smoothing, where a value of J=4 indicates 16-beat smoothing, J=3 indicates 8-beat smoothing, and so on. Blue error bars are the daytime Holder coefficients for the CHF patient whose data is shown in FIGS. 2a–c and 3a–c. The red error bars are the daytime Holder coefficients for a typical healthy individual. All other measurement parameters, such as the prefiltering method of prior art and scaling range, were unchanged.

FIG. 4a clearly shows the increased ability of the MF Holder coefficient to separate healthy from CHF patients, with increased smoothing. The CHF MF Holder coefficient increases steadily, but the MF Holder coefficient for the healthy individual does not. FIG. 4a demonstrates that a 1% abnormal beat frequency correlates with a serious overlap of normal and CHF error bars, even after prefiltering (J=0). Progressively increased wavelet smoothing according to the preferred embodiment of the invention, however, sequentially increases the separation of healthy from CHF data. It is thus logical to conclude that this overlap between healthy and CHF data Holder coefficients is due to the effect of the abnormal/arrhythmic beats exhibited by the patient, which results in an artificially low range of Holder coefficients. As the degree of smoothing increases, there is now a sharper distinction between the CHF patient and the healthy control patient, as would be expected for a typical CHF patient without abnormal/arrhythmic beats. We found by empirical analysis that 8-beat smoothing (J=3) gave the optimal separation between the Holder coefficient ranges of CHF patients and healthy patients, with minimal disruption of the multifractal cascade. More smoothing is possible, but this requires snapshots longer than 4096 beats, with subsequent loss of temporal resolution.

Figure 4B:
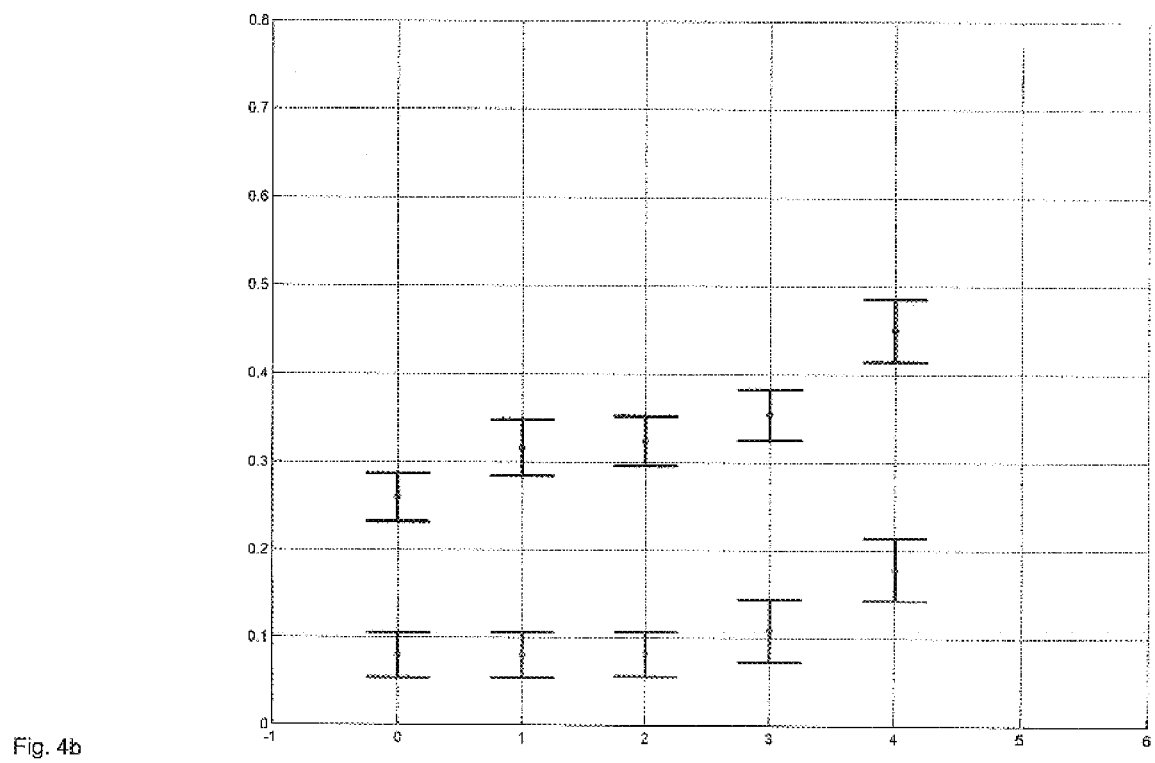
FIG. 4b is a graph illustrating the effect of progressively increased discrete wavelet smoothing on the daytime MF Holder coefficient on a CHF patient without abnormal beats.

FIG. 4b is a plot similar to FIG. 4a, except that in this case the 24-hour Holter monitor CHF patient data has no appreciable abnormal/arrhythmic beats (0.0005%, or 7 out of 57,000). Again, all analytic parameters are fixed except for the degree of wavelet smoothing. As anticipated on the premise that the abnormal beats adversely affect the MF Holder coefficient, the wavelet smoothing does not increase the separation of CHF and healthy data Holder coefficients.

This same general pattern shown in FIGS. 4a and 4b held true for all 32 CHF and 15 CAD patients examined as part of our study. This is an important result, since it demonstrates that the wavelet smoothing can be used on all patients—whether abnormal/arrhythmic beats are present or not—before performing the multifractal analysis. In other words, the application of this highly specialized EKG data smoothing technique only raises the Holder coefficients of CHF patients with abnormal beats, and not those of CHF or healthy patients that do not have abnormal/arrhythmic beats. This supports our premise that the abnormal beats introduce a non-fractal component into the multifractal Holder analysis, even when the scaling region of 16 beats or less is ignored. In addition, we have experimentally determined that only CHF patients with 1% or more abnormal/arrhythmic beats can have distorted Holder coefficients, which are enhanced by 8-beat wavelet smoothing. The fact that this smoothing greatly enhances the sensitivity and specificity of the Holder analysis, as well as raises most of the CHF Holder coefficients into the reported range for CHF patients without abnormal beats, supports our premise.

Figure 4C:
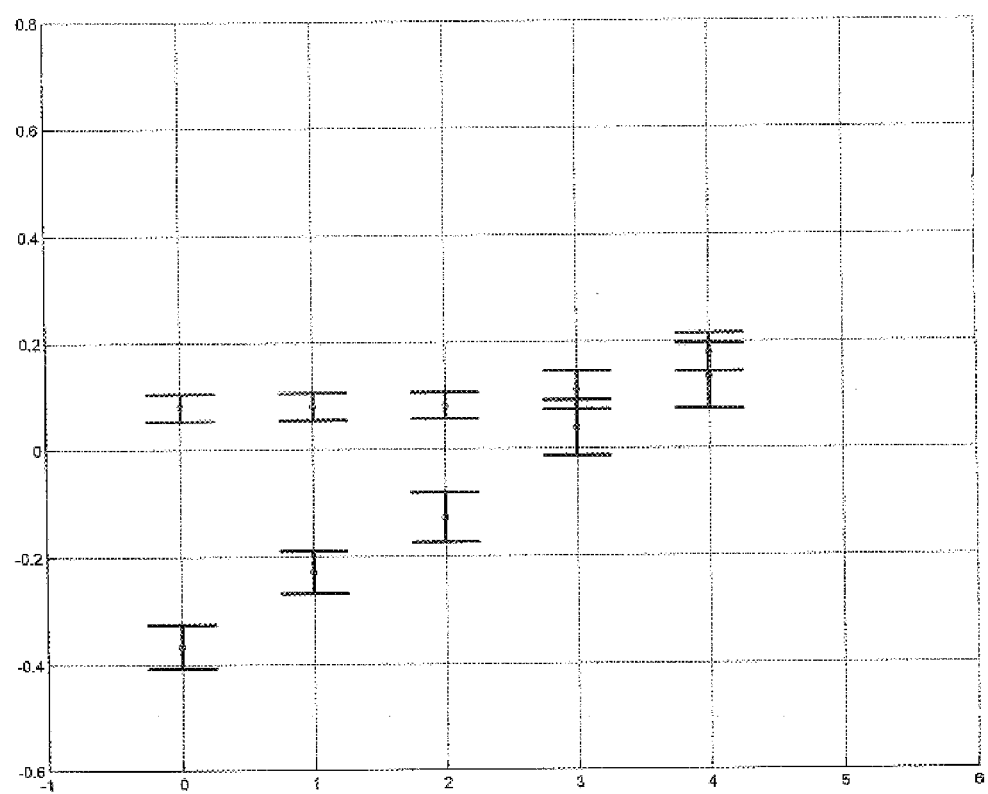
FIG. 4c is a graph illustrating the effect of various degrees of our discrete wavelet smoothing on the daytime MF Holder coefficient on a patient with 10% abnormal beats.

It should also be noted, however, that some patients have a steadily rising MF Holder coefficient with sequentially increased wavelet smoothing, but MF Holder coefficients remain in the normal range. FIG. 4c is a plot similar to FIGS. 4a and 4b, except that in this case the CHF patient has very severe arrhythmias, with approximately 10% abnormal/arrhythmic beats in the 24-hour time series. The patient's raw, unsmoothed heart rate varied abruptly from 50 to 150 beats virtually throughout the entire time series due to the presence of the abnormal beats (raw data not shown). Note the initial highly negative MF Holder coefficient of −0.4 in FIG. 4c, not seen in arrhythmia-free CHF patients, and the steady rise with increased smoothing. Such negative MF Holder coefficients are common in CHF or CAD patients with abnormal beats, but are not seen in heart disease or heart failure patients that do not have abnormal beats. In this case, even 16-beat wavelet smoothing does not fully remove the effect of this profound abnormal beat/arrhythmia effect on the calculation of the MF Holder coefficient. Also, an asymptotic limit is not reached, as one would expect if the abnormal beat effect had been completely removed. Furthermore, our examination of the 16-beat wavelet-smoothed EKG heart rate time series still shows abnormal beat effects (data not shown). These results support the need for further smoothing of some kind prior to multifractal analysis.

One possible method to resolve the problem evident in FIG. 4c is to increase the snapshot size to greater than 4096 beats, which would permit a greater degree of wavelet smoothing. It is likely, however, that the severe arrhythmias of a few patients will still be such that even this higher level of smoothing would not generate valid Holder coefficient ranges. It is for this reason that a preferred embodiment of the present invention includes other techniques to examine and identify patients where this problem occurs, such as the Levy flight anomalous beat and beat cluster detection method described below, and the multifractal alpha technique. Also, according to a preferred embodiment of the present invention, the wavelet smoothing performed on this data could be used in conjunction with probability density function (PDF) analysis which, as described below, can also be effective in reducing the sensitivity of the multifractal Holder coefficients to abnormal/arrhythmic beats.

Referring again to FIG. 16, we determine from our Levy flight analysis at block 102 whether the number of abnormal beats is greater than 5%, shown as blocks 112 and 114. If the number of abnormal beats is in fact greater than 5%, then we proceed to perform a MF alpha analysis only at block 116 (this process is explained below). If the number of abnormal beats is less than 5%, then we may perform both the MF alpha analysis at block 120 and the wavelet smoothing at block 124 as previously described.

After the wavelet smoothing step at block 124, the multifractal cascade coefficient (MFCC) is determined for the data at block 126. The calculation of MFCC has already been described in detail above. Also as previously described, a value of MFCC equal to or below the critical value indicates that heart disease is likely for the patient, shown at block 128. Conversely, a MFCC value greater than the critical value indicates that the patient may be free of heart disease at block 130. Also, however, this second result may indicate that inadequate smoothing has been performed on the data.

In addition to the calculation of the MFCC at block 126, we may also perform MF Holder sequential wavelet smoothing at block 132. Again, the details of this process have been described above. If the result of this calculation is an MF Holder value that rises with increased smoothing steps as illustrated by block 134, then a MF Holder value greater than or equal to the critical value indicates heart disease at block 138, but a value that is less than the critical value is not necessarily determinative at block 140. On the other hand, if the MF Holder value does not rise with increased smoothing steps as illustrated by block 136, then we have determined that a value of the MF Holder that is less than the critical value is determinative of a healthy patient at block 144, and, just as in the case where the MF Holder rises, a MF Holder value greater than or equal to the critical value is indicative of heart disease at block 142.

(e) Determination and Validation of the Short Term (ST) MF Alpha Coefficient

We will next describe the method for determining of the multifractal (and monofractal) alpha coefficients to characterize the 1–8 beat region according to a preferred embodiment of the present invention. This differs from the more conventional MF Holder analysis in that the focus is not on the fractal region for scales longer than 8–16 beats, but rather on the less than 8-beat region. For example, prior art monofractal DFA alpha studies focused only on the <11 beat region. Turning to FIG. 16, blocks 116 and 120 show the MF alpha analysis performed for patients with 5% or more abnormal beats, and less than 5% abnormal beats, respectively. In each case, a result of a MF alpha coefficient less than or equal to the critical value at block 118 is an indication of heart disease, while a result of a MF alpha coefficient that is greater than the critical value at block 122 is an indication of a healthy patient. The method for determining the critical MF alpha coefficient value is described herein.

FIGS. 9a–g show the results of the calculation of the monofractal and multifractal alpha coefficients on a single 4096-beat snapshot for a patient with 3% abnormal beats. What is significant about this method is that the region we analyzed is the 1–4 beat region, which was expressly ignored in the multifractal Holder analysis. Here, however, we focus on this region, and expand on the monofractal STalpha analysis described in the prior art by those who used a longer beat interval region. The monofractal alpha is a scaling of the variance of the discrete wavelet transform in the beat scale range of interest. The analogous multifractal scaling coefficient would be the variance of the CWT, that is, the value of the multifractal Holder coefficient for $q=2$, again over the same scaling range, which in our case is a range of 1–4 beats. We have used the MF Holder mathematical formalism to define $H(q=2)$. All that is necessary for the calculation of the multifractal alpha coefficient is to calculate $H(q=2)$ in the 1–4 beat scaling range for each snapshot, and then add ½.

Figure 9:
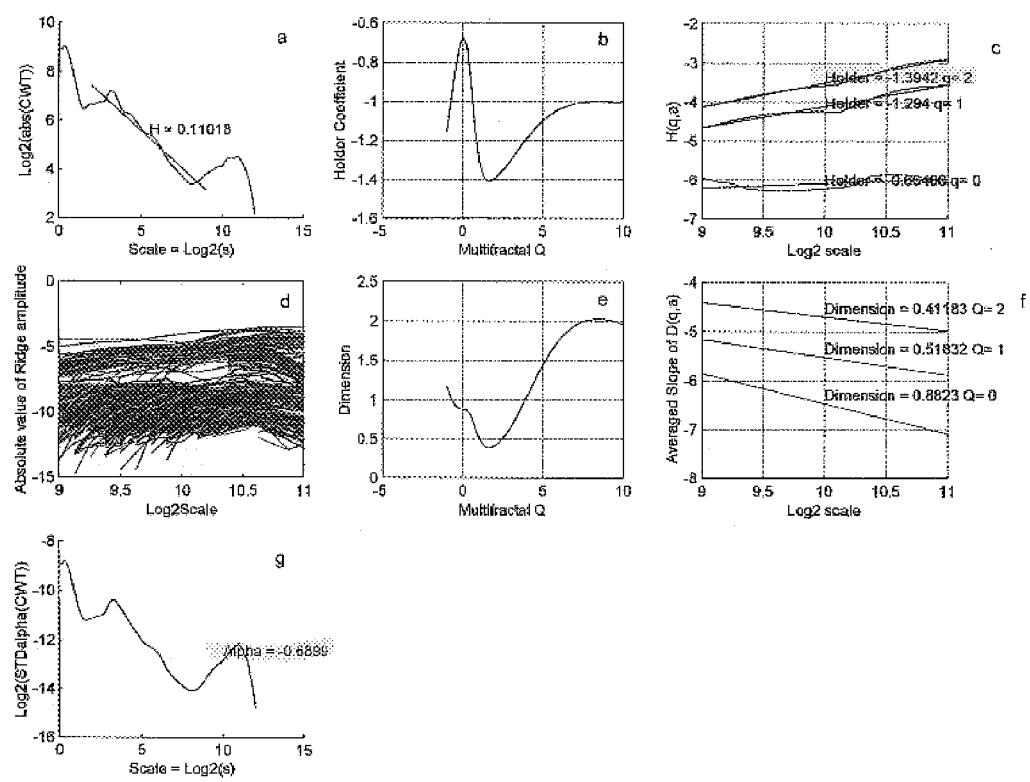
FIG. 9a shows the monofractal Holder coefficient determination for a single 4096-beat EKG snapshot of a patient with 5% abnormal beats, which will be used to demonstrate the calculation of the MF alpha.
FIG. 9b shows H(q), which is only valid for q>0 for the method used in calculating the MF alpha scaling coefficient, where H(q=2) is the multifractal equivalent of the monofractal alpha.
FIG. 9c shows the determination of H(q, a) for the multifractal alpha calculation, q>0 only, where the MF scaling range was a narrow 1–4 beats.
FIG. 9d shows the wavelet ridges for the snapshot of FIG. 9a, where the two populations represent the normal ridges and the abnormal beat ridges.
FIG. 9e depicts the MF dimension D(q) for the monofractal 4096-beat snapshot valid for values of q>0 only.
FIG. 9f is a graph illustrating the determination of the MF dimension D(q, a) for the monofractal 4096-beat snapshot for the selected scaling range shown, valid for q>0 only.
FIG. 9g shows the monofractal alpha determination of −0.6899 by wave variance method, determined from the log2—log2 slope of the CWT in the 1–4 beat scaling region shown.

FIG. 9a shows the determination of the monofractal Holder coefficient, and the scaling range (straight black line) over which it is calculated, which as can be seen from the figure does not overlap the scaling range for the determination of alpha. Here, log2 scales 2–9 are used. It may be noted that the CWT peaks at short beat intervals, reaching an absolute peak at single-beat resolution, which is characteristic of a patient with abnormal beats.

FIG. 9d shows the wavelet ridges used in the calculation, over the log2 scaling range of 9–11 (1–4 beat resolution). This scaling range was determined empirically for optimal contrast between normal and abnormal (CHF and CAD) patients, and then was locked in for all future data analysis. FIG. 9g shows the determination of the monofractal alpha coefficient over the 9–11 log2 scale (1–4 beats) as a straight black line. For comparison, it may be noted that prior STalpha work was done with a slightly different scaling range, and with DFA, or discrete wavelet transform methods, not with the CWT. Our monofractal STalpha coefficient is −0.6899.

The multifractal alpha scaling coefficient is shown in FIG. 9c, which is the same graph as the MF Holder $H(q, a)$ graph. $H(q, a)$ in this case is determined from the wavelet ridges in the same manner as the MF $H(q, a)$ determinations, with the exception that the wavelet ridge "sup" step is not incorporated. This means that values of $H(q, a)$ for negative q are invalid, but we are only interested in $q=2$ anyway, which corresponds to the wavelet variance with the monofractal alpha. We also choose the log2 (dyadic) scaling range of 9–11 for alpha, rather than the usual much broader Holder scaling range. In this case we are not interested in the multifractal cascade $D(H(q))$, but only $H(q=2)$, so the additional information for different values of q in FIGS. 9e and 9f is ignored, in contrast to the MF Holder analysis of 5e, 5f, 6e, and 6f. H(q=2)+½ can be shown to be the multifractal equivalent of the monofractal alpha of prior art. H(q=2) has a value of −1.3942 from FIG. 9c, and thus the MFAlpha coefficient is −0.8942 (H(q=2)+½). This value is somewhat more negative than the monofractal alpha of −0.6899 for this snapshot. Despite this difference, analysis of the 47 CAD plus CHF patients, and the 12 healthy control patients, reveals that on average our MF Alpha and our monofractal Alpha are quite similar in what they detect. Our ROC analysis of the MF Alpha demonstrates that it is much more effective than our monofractal alpha method at separating healthy from CAD/CHF patients. Our monofractal alpha method has sensitivity and specificity comparable to published results using DFA, and wavelet STalpha analysis. Also, our overlapping MF alpha analytic method does not need as long a snapshot length for the same statistical significance. This latter point will be useful in clinical applications, since less data will need to be collected.

Figure 10:
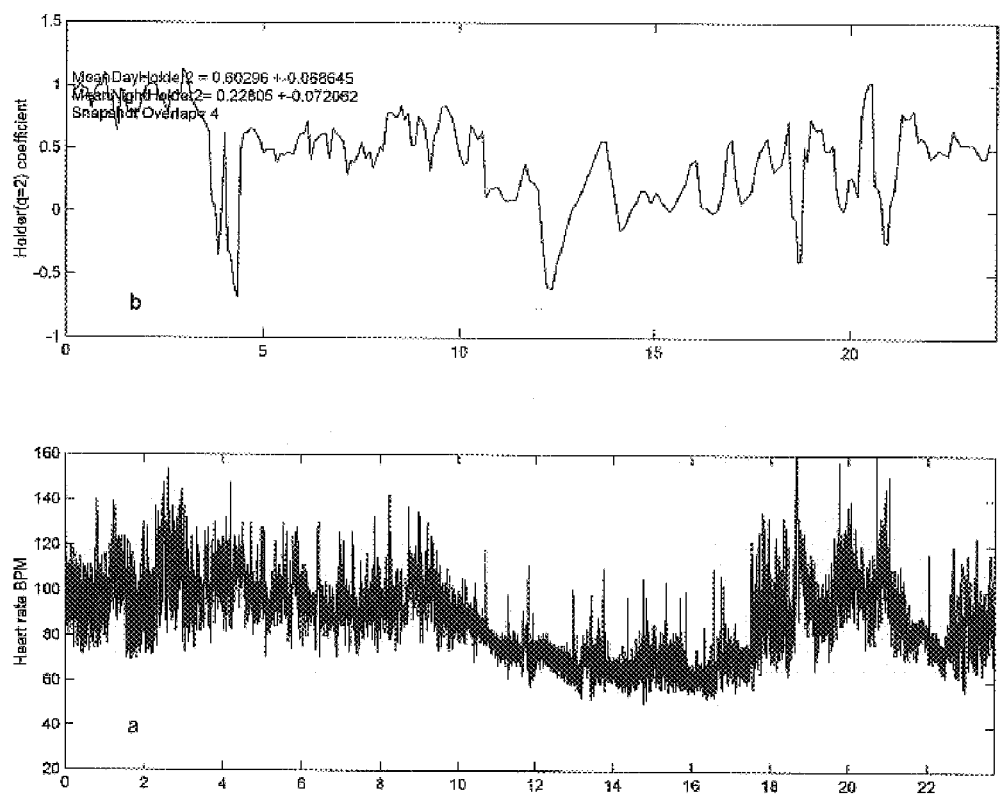
FIG. 10a shows a 24-hour EKG time series for a normal subject without smoothing.
FIG. 10b shows H(q=2) for the time series of FIG. 10a, used for determination of the MF alpha, 0.67% prefiltered and unsmoothed, where MF alpha is given by MF H(q=2)+ ½, over the chosen scaling region of 1–4 beats.
Figure 11:
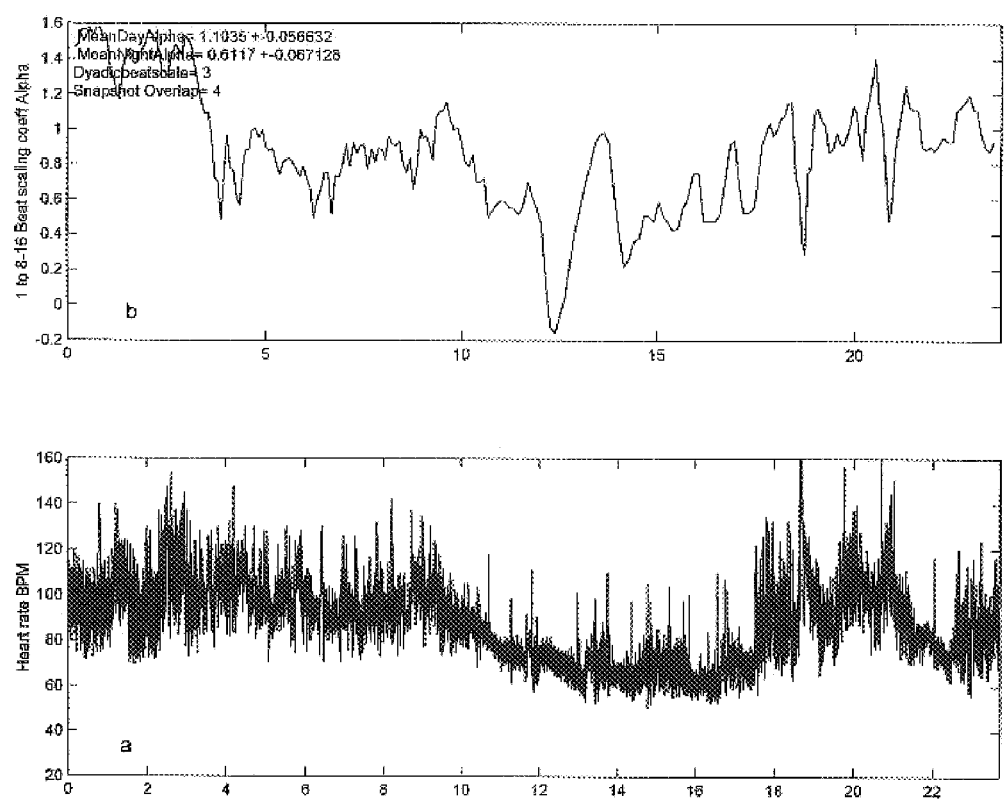
FIG. 11 shows the monofractal alpha time series for the same patient with data plotted in FIG. 10a, over the same scaling range of 1–4 beats.

FIG. 10a shows the time dependence of the multifractal alpha (calculated as H(q=2)+½) for a normal control. The daytime multifractal alpha was 1.1030. FIG. 11 illustrates the time dependence plot of the monofractal alpha coefficient for a normal control based on the time series of FIG. 10a. The daytime monofractal alpha was 1.1035, in good agreement with the daytime MF alpha. It should also be noted that the general time dependence of the multifractal alpha and monofractal alpha are quite similar. The close agreement of mono- and multifractal alpha is less evident in patients with significant numbers of abnormal beats, presumably due to the fact that the MF alpha detects slightly different aspects of the time series phenomena when compared to the monofractal case.

Figure 12A:
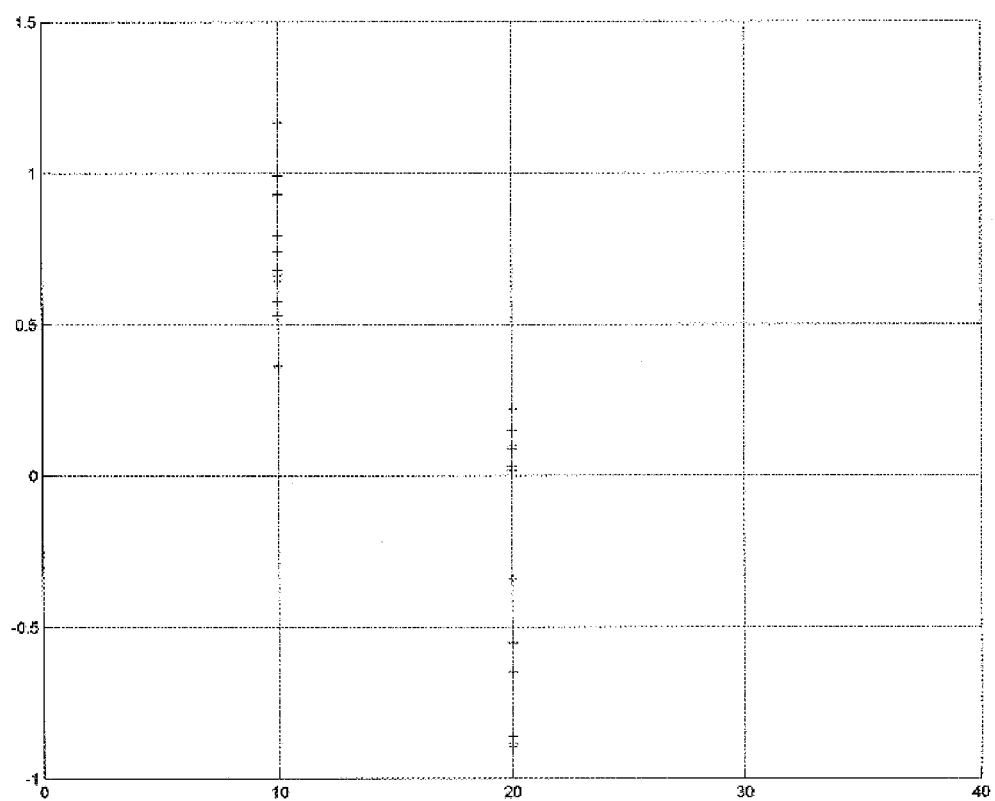
FIG. 12a is a histogram illustrating the raw CHF/normal MF alpha data from our study without wavelet presmoothing.
Figure 12B:
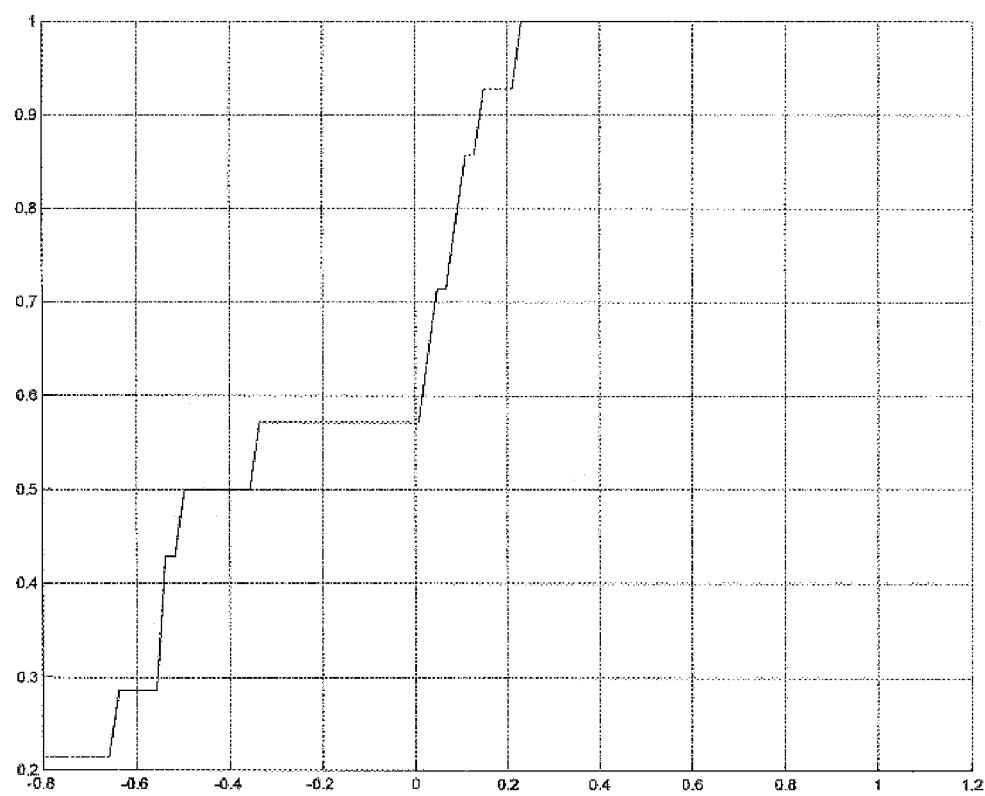
FIG. 12b is a chart illustrating the diagnostic sensitivity of our results comparing CHF and normal patients for the multifractal alpha.
Figure 12C:
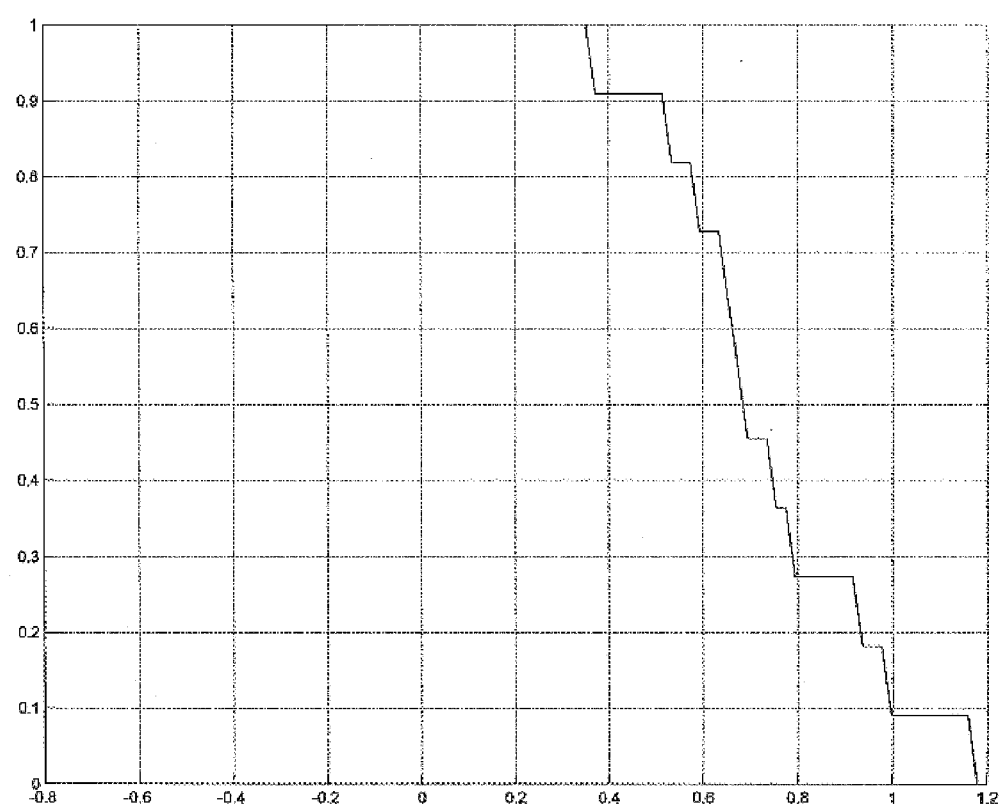
FIG. 12c is a chart illustrating the diagnostic specificity of our results comparing CHF and normal patients for the multifractal alpha.
Figure 12D:
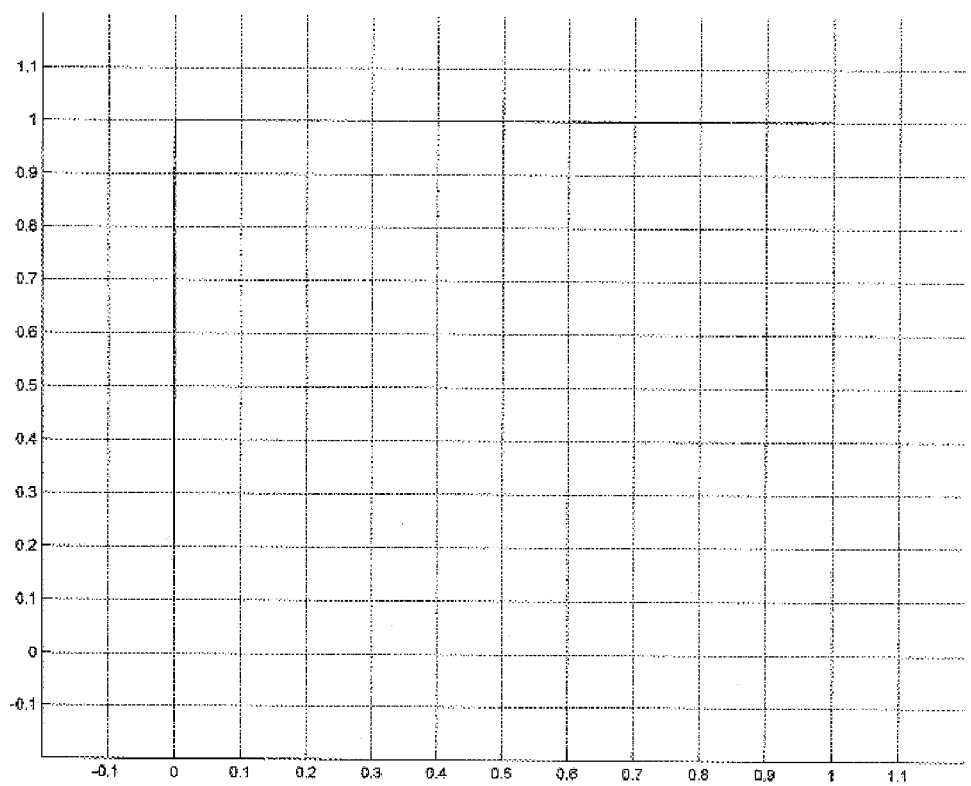
FIG. 12d is the daytime Receiver Operating Curve (ROC) for our multifractal alpha analysis, showing a perfect separation of CHF from normal patient data (sensitivity and specificity of 100%).
Figure 13A:
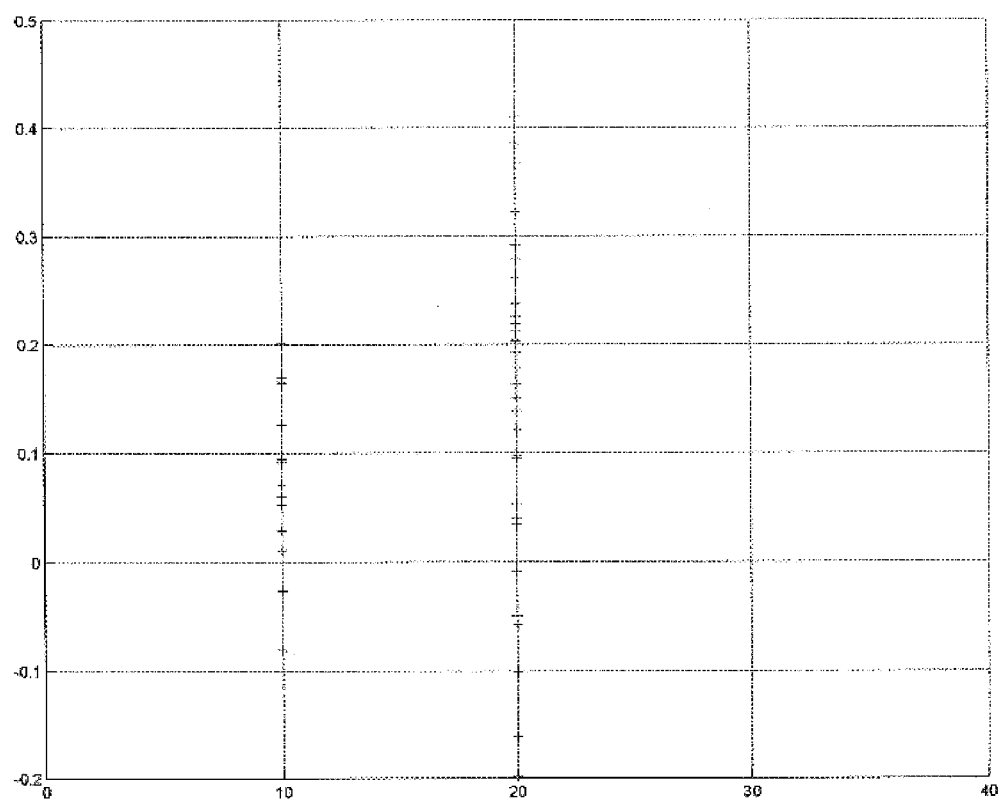
FIG. 13a is a histogram illustrating the raw CHF/normal monofractal alpha results without wavelet presmoothing based on the same data used in FIGS. 12a–d.
Figure 13B:
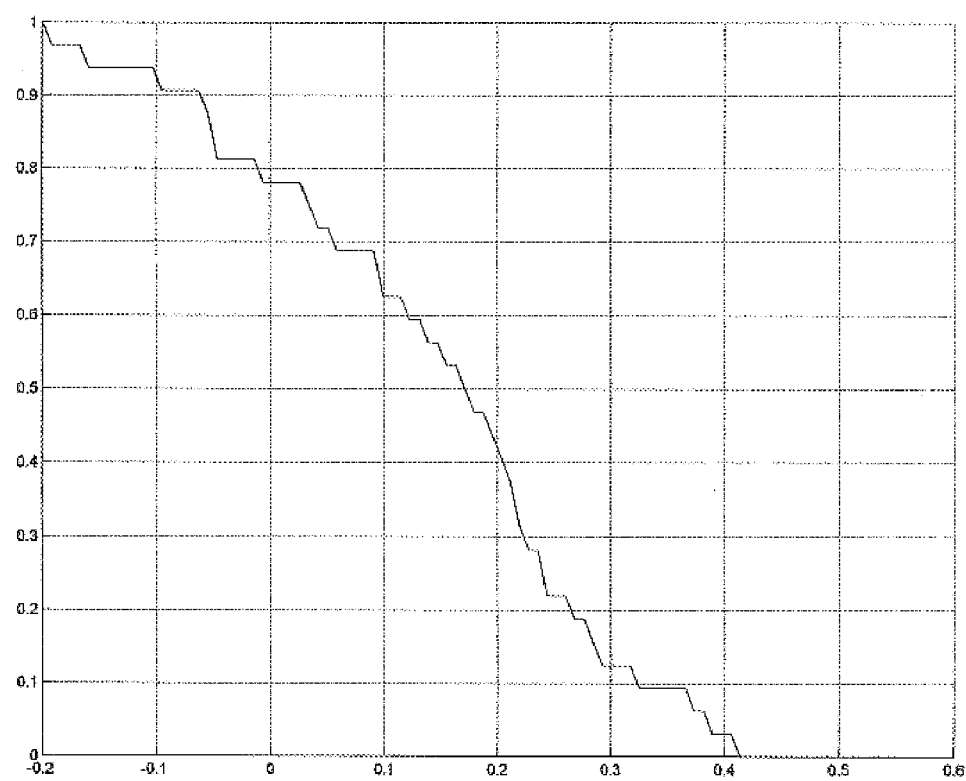
FIG. 13b is a chart illustrating the diagnostic sensitivity of the results of comparing CHF and normal patient data for the monofractal alpha.
Figure 13C:
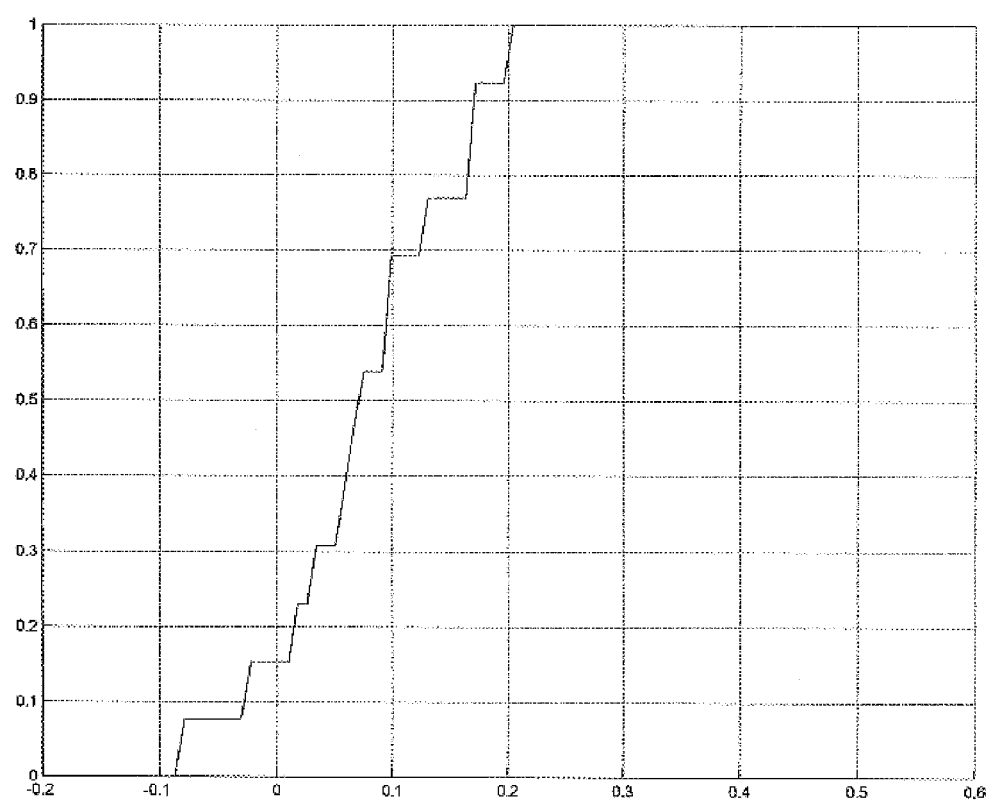
FIG. 13c is a chart illustrating the diagnostic specificity of the results of comparing CHF and normal patient data for the monofractal alpha.
Figure 13D:
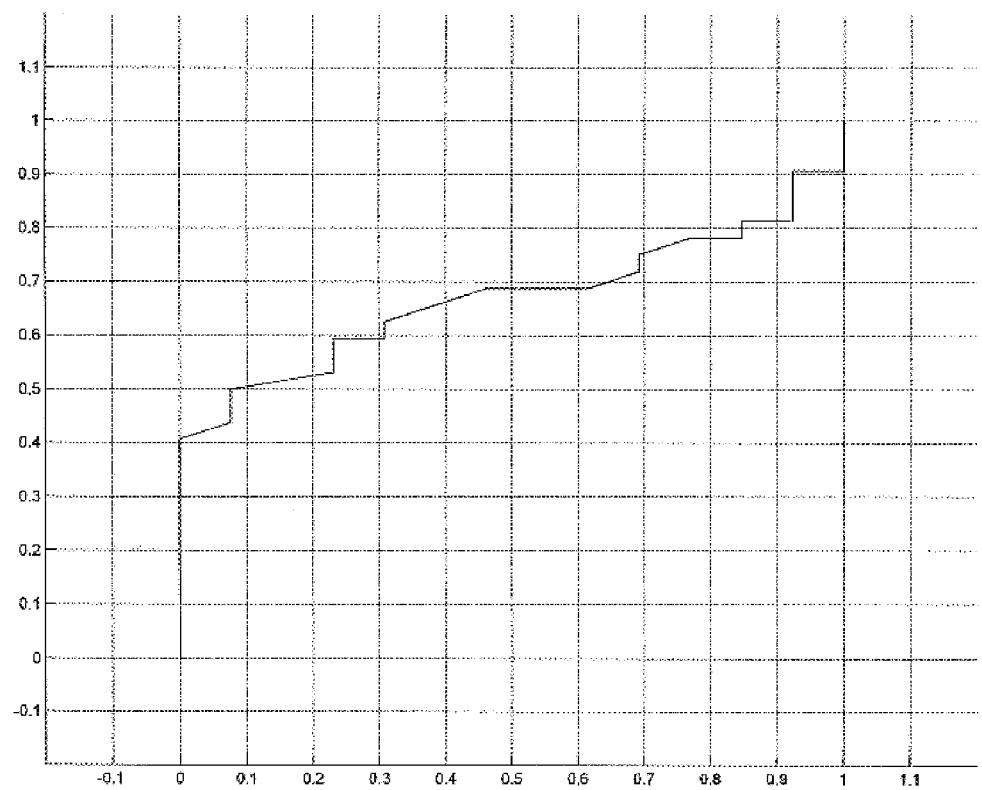
FIG. 13d is the daytime Receiver Operating Curve (ROC) for the monofractal alpha analysis.
Figure 14A:
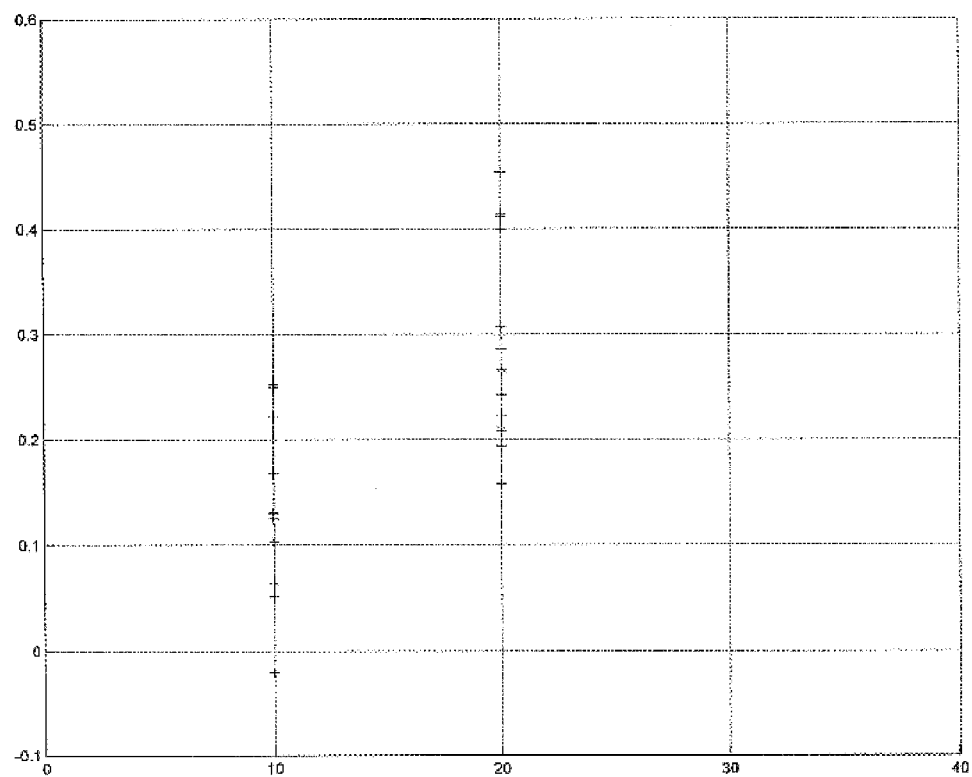
FIG. 14a is a histogram illustrating the CHF/normal MF alpha results with 8-beat wavelet presmoothing based on the same data used in FIGS. 12a–d.
Figure 14B:
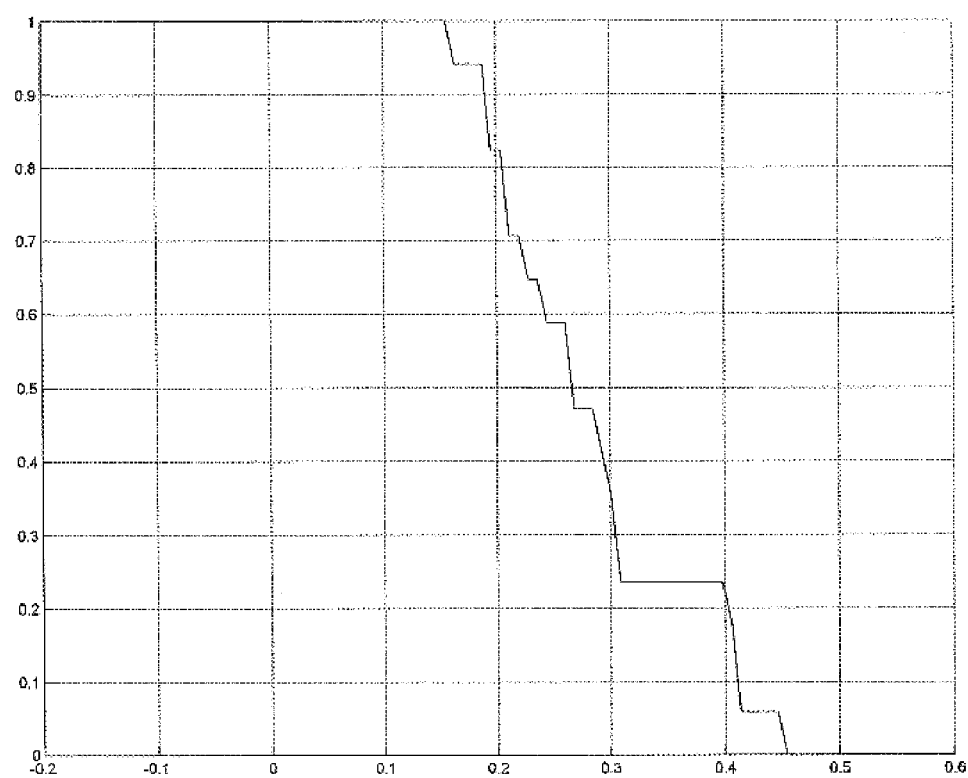
FIG. 14b is a chart illustrating the diagnostic sensitivity of the results of comparing CHF and normal patient data for the MF alpha with presmoothing.
Figure 14C:
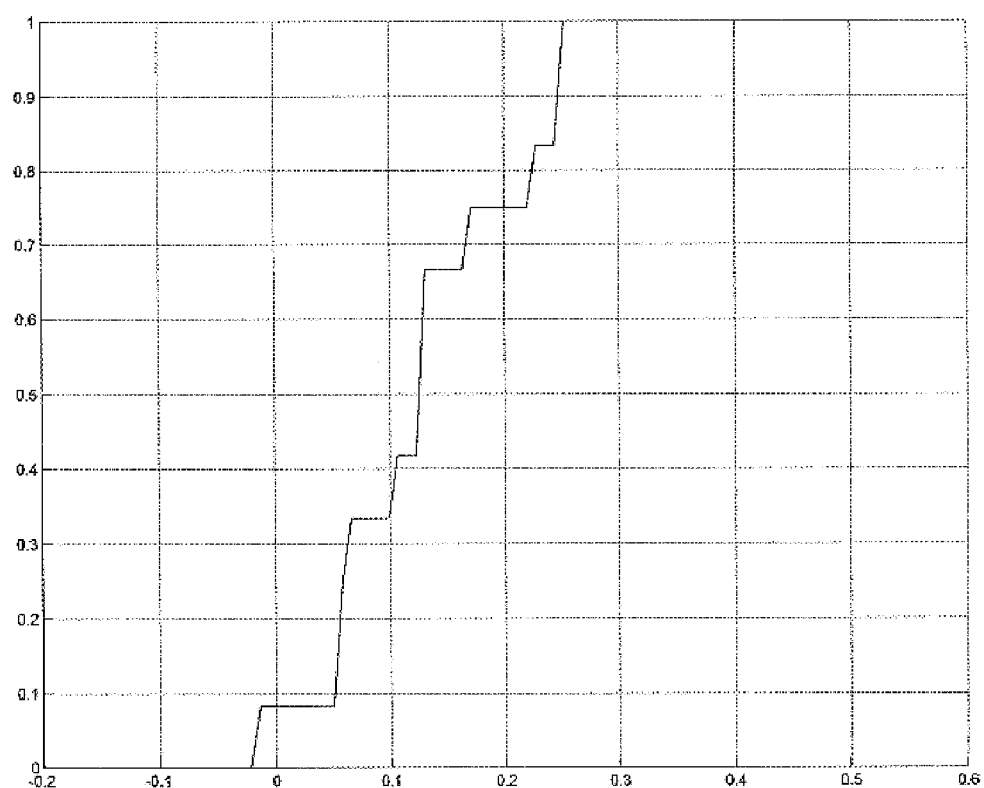
FIG. 14c is a chart illustrating the diagnostic specificity of the results of comparing CHF and normal patient data for the MF alpha with presmoothing.
Figure 14D:
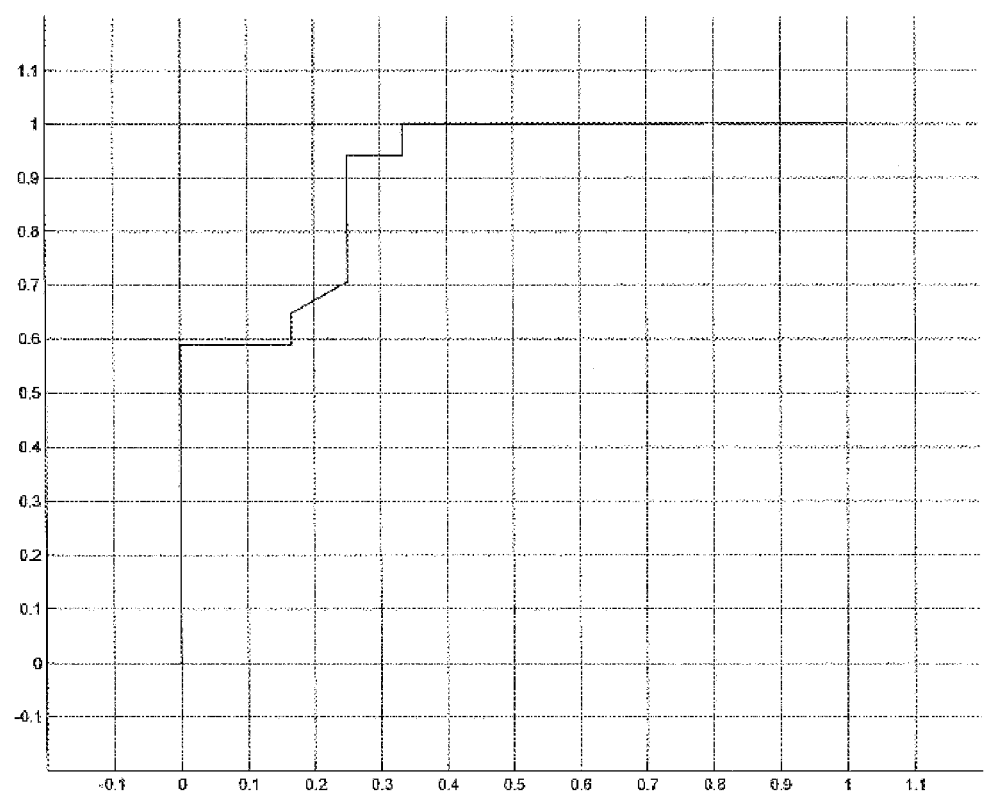
FIG. 14d is the daytime Receiver Operating Curve (ROC) for the MF alpha analysis with presmoothing.
Figure 15:
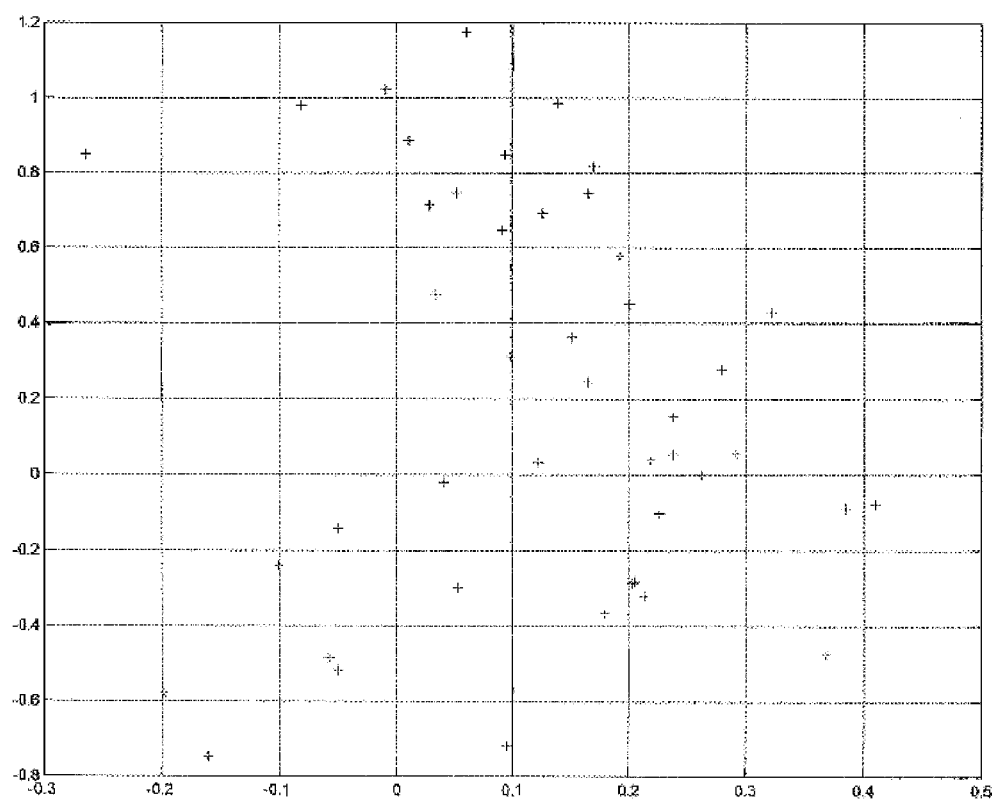
FIG. 15 shows a 2-d plot of monofractal ST alpha vs monofractal (unsmoothed) Holder for our CHF patient population, illustrating the improved diagnostic separation quality when compared to alpha or Holder alone.

A MF alpha comparison of 37 CHF patients and 12 normals is shown in FIGS. 12a–c, showing excellent separation of normal from abnormal. A ROC is plotted in FIG. 12d, revealing 100% sensitivity and 100% specificity. We also determined a ROC for a comparable monofractal alpha analysis of our same patient population, and determined that a reduced sensitivity and specificity was evident, very similar to published values for the DFA STalpha (this data is not shown). Thus it seems that our analysis of MF alpha confirms its value as a diagnostic improvement over the prior art, which was based on simpler monofractal methods.

FIGS. 13a–d shows the ROC for our unsmoothed monofractal Holder CHF determination, showing 63% sensitivity, and 69% specificity. One may note the poor sensitivity and specificity, due partially to the lack of wavelet smoothing, which removes the effects of abnormal beats from the time series. If only abnormal beat-free CHF patients are included, the sensitivity is 91%, and the specificity 75%.

FIGS. 14a–d shows the ROC for our 8-beat smoothed daytime MF Holder CHF vs normal determination, showing 82% sensitivity and 75% specificity. All patients and controls were analyzed with the same smoothing step before MFA. This is a considerable improvement over the unsmoothed MF Holder analysis, indicating that the wavelet smoothing step is very important. We should point out that examination of sequential smoothing analysis, and direct examination of the smoothed time series, revealed that not all patients had enough smoothing to completely eliminate anomalous beat effects. Thus it is likely that with better methods of removing the adverse effects of the abnormal beats, the MF Holder sensitivity and specificity could be further increased.

3. Alternative Techniques (a) Use of the Probability Distribution Function (PDF)

There are several ways to remove the effects of abnormal beats (that is, events that create intermittency), which disrupt the MF Holder analysis. As noted above, the prior art method of prefiltering may be applied to remove isolated (unclustered) anomalous or abnormal beats if they consist of no more than 2% of the total beat population. The problems with this method are that there are no well-defined rules as to how many beats can be removed without altering the properties of the time series, and (as we have shown) if the abnormal beats are strongly clustered, their intermittency effect can be much worse. If the abnormal beats are unclustered and more than 2%, or even 1% abnormal but intensely clustered (for examples, see FIGS. 2a–c and 3a–c), the MF Holder may be adversely affected.

In addition to the wavelet smoothing method described above, the present invention comprises the use of a probability distribution function (PDF) as part of the multifractal Holder coefficient analysis, which may offer a different perspective from conventional MF Holder analysis. The MF Holder coefficient can be determined directly from the scaling of the PDFs, which are determined from the wavelet ridges. This calculation is described generally, for example, in W. L. Hwang et al., supra; N. Decoster et al., "A Wavelet-Based Method for Multifractal Image Analysis. II. Applications to Synthetic Multifractal Rough Surfaces," The European Physical Journal B 15, 739–764 (2000); and S. G. Roux et al., "A Wavelet-Based Method for Multifractal Image Analysis. III. Applications to High-Resolution Satellite Images of Cloud Structure," The European Physical Journal B 15, 765–786 (2000), each of which are incorporated herein by reference. Calculation of the full multifractal formalism is not necessary using this technique. Using self-similar scaling relationships for scale a and moment parameter q, the MF Holder coefficient can be determined directly instead of from Z(q, a) or Tau (q, a). We have performed this process on a few patients, but we expect that the PDF approach to direct calculation of the MF Holder coefficient will be less sensitive to intermittency effects, because the abnormal beats will generally be in the tail of the PDF, and not in its central body. If the tail is ignored during the self-similar analysis utilized to calculate the Holder coefficient, the effect of the abnormal beats will be minimized. We believe that more complete studies will demonstrate that a PDF approach to the self-similar determination of the MF Holder coefficient can effectively separate healthy and heart disease patients even in the presence of a significant number of abnormal beats.

To perform the calculations necessary for the PDF analysis, the probability distribution function for scale a (PDFa) is first to be determined from the time series (RR-interval dataset) wavelet ridges for individual scaling ranges a. Plots of PDFa can be overlapped for different a scales, and the PDFa normalized with the correct choice of Holder coefficient for the chosen scaling range a. The following graphical relation is used to determine the self-similarity of the PDFa's:

$$a^{-qH} M^q \, PDFa(M) \qquad (1)$$

versus the parameter $$M/a^H. \qquad (2)$$

Here M is the ridge amplitude of the wavelet band at scale a, PDFa(M) is the probability of that amplitude at scale a, and H is the Holder coefficient, which may depend on the moment parameter q. The result of such analysis is that if the q and scale-normalized PDFa curves can be made to overlap, the PDFa values are therefore self-similar, and can be used to determine H(q) (more precisely, one could say that the PDFa values are self-affine). The original time series would thus be self-affine with Holder coefficient H(q). In practice, only certain key ranges of a and q may show this self-affine property. In addition, only H(q=0) is needed to determine the MF Holder coefficient.

(b) Selective Ridge Removal

An alternative approach to calculate the parameters described herein is based on the disclosure in Z. R. Struzik, "Direct Multifractal Spectrum Calculation from the Wavelet Transform," Centrum voor Wiskunde en Informatica, INS-R9914 (Oct. 31, 1999), which is incorporated herein by reference. This approach allows for the calculation of the Holder coefficients directly from a ridge map, so that the thermodynamic multifractal partition coefficient calculations described above are not required. The approach thus allows for the removal of offending (that is, anomalous) wavelet ridges, if the interfering intermittent process is understood. If this removal of intermittency is done carefully, the MF Holder analysis and MF alpha analysis may be greatly improved. We believe that one or both of these two methods will prove to be effective in a clinical setting when used in connection with or in lieu of our wavelet smoothing approach to solving the problem of abnormal beat intermittency effects.

(c) Calculation of Tsallis Entropic Coefficients, Lyupanov Exponents, and Various Types of Entropy Several types of entropy, Lyapunov exponents, and Tsallis entropic scaling coefficients can be determined directly from the MF Holder analysis. For example, approximate Entropy (ApEn) already appears to have clinical utility in estimating complexity of a EKG series. We believe that these other parameters may also be of clinical importance in the diagnosis and prognosis of cardiac conditions.

Several versions of entropy come immediately from the multifractal formalism. The Shannon entropy or information dimension can be readily determined for q=1, and formulas exist for the Pesin metric and topological entropies. These calculations are explained in L. Barreira et al., "Dimension and Product Structure of Hyperbolic Measures," Annals of Mathematics (2) 149 (1999), 755–783; L. Barreira et al., "Variational Principles and Mixed Multifractal Spectra," Transactions of American Mathematics Society 353 (2001), 3919–3944; V. Latora et al., "The Rate of Entropy Increase at the Edge of Chaos," Physics Letters A 273 (2000) 97–103; Y. Pesin et al., "Dimension Theory in Dynamical Systems: Contemporary Views and Applications. xii," 304 p. 1997 Series: (CLM) Chicago Lectures in Mathematics Series; L. Barreira et al., "On a General Concept of Multifractality: Multifractal Spectra for Dimensions, Entropies, and Lyupanov Exponents. Multifractal Rigidity," Chaos (1997), no. 1, 27–38; H. E. Hentschel et al., "The Infinite Number of Generalized Dimensions of Fractals and Strange Attractors," Physica D 8(3):435–444 (1983); Y. Pesin et al., "The Multifractal Analysis of Gibbs Measures: Motivation, Mathematical Foundation and Examples," Chaos 7 (1997), no. 1, 89–106; and P. Grassberger et al., "Dimensions and Entropies of Strange Attractors from a Fluctuation Dynamics Approach," Physica D 13(1–2):34–54 (1984), each of which is hereby incorporated by reference. Local and non-local Lyupanov exponents can also be determined using the method of Prasad, as explained in A. Prasad et al., "Characteristic Distribution of Finite-Time Lyapunov Exponents," Physical Review E Vol. 60, No. 3 September 1999:2761–2766, which is incorporated herein by reference. For a one dimensional system such as an EKG RR-interval series, the Komolgorov-Sinai entropy can be calculated directly and is the same as the Lyupanov coefficient, as explained in P. Grassberger et al., "Estimation of the Komolgorov Entropy from a Chaotic Signal," Physical Review A 28:2591–2593 (1983), which is hereby incorporated by reference. Lastly, we believe there is clinical utility of the Tsallis entropic scaling coefficient q*, which has been shown to characterize the properties of near-equilibrium fluctuation properties of the attractor, where the Lyupanov coefficient is usually near zero and hence plays a minimal role. The entropic scaling coefficient q* is determined by 1/Hmin–1/Hmax, where d(H min) and d(Hmax) are the limits of the multifractal dimension spectrum determined from multifractal analysis described above, as explained in U. Tirnakli et al., "Generalization of the Kolmogorov-Sinai Entropy: Logistic and Periodic-Like Dissipative Maps at the Chaos Threshold," Los Alamos arXiv:cond-mat/0005210 v1 May 12, 2000 (originally published at International Workshop on Classical and Quantum Complexity and Nonextensive Thermodynamics, Proceedings (2000)), which is incorporated herein by reference.

In summary, we have extensively analyzed the MF Holder coefficient in 12 healthy patients, 35 CHF patients, and 12 CAD patients, and have determined that the Daubechies 8 MODWT 8-beat smoothing step can significantly increase the separation of healthy versus CHF/CAD patient MF Holder coefficients. Severe cases of abnormal beats/arrhythmias can be shown to have negative Holder coefficients well below the expected Holder level for healthy patients, and rise into the expected level for CHF patients on sequentially increased smoothing. Our smoothing process removes scales outside the scaling region of 16–2048 beats used in the calculation of the MF Holder coefficient, but even then the smoothing is still very important. Patients without abnormal beats are not significantly affected by the wavelet smoothing step, strongly supporting the validity of our smoothing method.

The present invention has been described with reference to certain preferred and alternative embodiments that are intended to be exemplary only and not limiting to the full scope of the present invention as set forth in the appended claims.

What is claimed is:

1. A method of predicting a patient's risk of sudden death from cardiac disease, comprising the steps of:
   (a) collecting electrocardiogram data;
   (b) smoothing the data by applying a wavelet transform filter to the data; and
   (c) applying wavelet-based multifractal analysis to the data.

2. The method of claim 1, wherein the step of applying multifractal analysis to the data comprises the step of calculating a multifractal predictive coefficient, wherein the predictive coefficient has a numerical value that correlates to the patient's risk of sudden death from cardiac disease.

3. The method of claim 2, wherein said step of calculating a multifractal coefficient comprises the step of calculating a multifractal Holder coefficient.

4. The method of claim 1, wherein said step of applying a wavelet transform filter comprises the step of applying a MODWT wavelet transform filter.

5. The method of claim 1, further comprising the step of performing a probability distribution on the data prior to the step of applying wavelet-based multifractal analysis.

6. The method of claim 1, further comprising the step of performing a cluster analysis to the data.

7. The method of claim 6, wherein said step of performing a cluster analysis comprises the step of performing a Levy flight cluster analysis.

8. The method of claim 1, further comprising the step of calculating a short-scale multifractal coefficient, wherein said short-scale multifractal coefficient characterizes the short-scale beat region of the data.

9. The method of claim 8, wherein said step of calculating a short-scale coefficient comprises the step of calculating a multifractal alpha coefficient.

10. The method of claim 9, wherein said multifractal alpha coefficient characterizes a scale of one of 1–4 to 1–16 beats.

11. The method of claim 1, further comprising the step of quantifying the multifractality of the data by generating a multifractal cascade coefficient.

12. The method of claim 11, wherein said step of quantifying the multifractality of the data includes the step of generating a quadratic coefficient, wherein the value of said quadratic coefficient is indicative of the degree of multifractality of the data.

13. The method of claim 12, wherein said quadratic coefficient is indicative of multifractal data when the quadratic coefficient has a value greater than a threshold value.

14. A method of determining the severity of cardiac disease, comprising the steps of:
(a) collecting electrocardiogram data;
(b) performing a probability distribution on the data; and
(c) applying wavelet-based multifractal analysis to the data.

15. The method of claim 14, wherein the step of applying multifractal analysis to the data comprises the step of calculating a multifractal predictive coefficient, wherein the predictive coefficient has a numerical value that correlates to the patient's risk of sudden death from cardiac disease.

16. The method of claim 15, wherein said step of calculating a multifractal coefficient comprises the step of calculating a multifractal Holder coefficient.

17. The method of claim 14, wherein said step of applying a wavelet transform filter comprises the step of applying a MODWT wavelet transform filter.

18. The method of claim 14, further comprising the step of applying a wavelet transform filter to the data prior to the step of applying wavelet-based multifractal analysis.

19. The method of claim 14, further comprising the step of performing a cluster analysis to the data.

20. The method of claim 19, wherein said step of performing a cluster analysis comprises the step of performing a Levy flight cluster analysis.

21. The method of claim 14, further comprising the step of calculating a short-scale multifractal coefficient, wherein said short-scale multifractal coefficient characterizes the short-scale beat region of the data.

22. The method of claim 21, wherein said step of calculating a short-scale coefficient comprises the step of calculating a multifractal alpha coefficient.

23. The method of claim 22, wherein said multifractal alpha coefficient characterizes a scale of one of 1–8 to 1–16 beats.

24. The method of claim 14, further comprising the step of quantifying the multifractality of the data by generating a multifractal cascade coefficient.

25. The method of claim 24, wherein said step of quantifying the multifractality of the data includes the step of generating a quadratic coefficient, wherein the value of said quadratic coefficient is indicative of the degree of multifractality of the data.

26. The method of claim 25, wherein said quadratic coefficient is indicative of multifractal data when the quadratic coefficient has a value greater than a specified threshold.

27. A method of diagnosing cardiac disease in a patient, comprising the steps of:
(a) collecting electrocardiogram data;
(b) smoothing the data by applying a wavelet transform filter to the data; and
(c) applying wavelet-based multifractal analysis to the data.

28. The method of claim 27, wherein the step of applying multifractal analysis to the data comprises the step of calculating a multifractal predictive coefficient, wherein the predictive coefficient has a numerical value that correlates to the presence of cardiac disease in the patient.

29. The method of claim 28, wherein said step of calculating a multifractal coefficient comprises the step of calculating a multifractal Holder coefficient.

30. The method of claim 27, wherein said step of applying a wavelet transform filter comprises the step of applying a MODWT wavelet transform filter.

31. The method of claim 27, further comprising the step of performing a probability distribution on the data prior to the step of applying wavelet-based multifractal analysis.

32. The method of claim 27, further comprising the step of performing a cluster analysis to the data.

33. The method of claim 32, wherein said step of performing a cluster analysis comprises the step of performing a Levy flight cluster analysis.

34. The method of claim 27, further comprising the step of calculating a short-scale multifractal coefficient, wherein said short-scale multifractal coefficient characterizes the short-scale beat region of the data.

35. The method of claim 34, wherein said step of calculating a short-scale coefficient comprises the step of calculating a multifractal alpha coefficient.

36. The method of claim 35, wherein said multifractal alpha coefficient characterizes a scale range of 1–4 to 1–16 beats.

37. The method of claim 27, further comprising the step of quantifying the multifractality of the data by generating a multifractal cascade coefficient.

38. The method of claim 37, wherein said step of quantifying the multifractality of the data includes the step of generating a quadratic coefficient, wherein the value of said quadratic coefficient is indicative of the degree of multifractality of the data.

39. The method of claim 38, wherein said quadratic coefficient is indicative of multifractal data when the quadratic coefficient has a value greater than a threshold value.

40. A method of diagnosing cardiac disease in a patient, comprising the steps of:
(a) collecting electrocardiogram data;
(b) performing a probability distribution on the data; and
(c) applying wavelet-based multifractal analysis to the data.

41. The method of claim 40, wherein the step of applying multifractal analysis to the data comprises the step of calculating a multifractal predictive coefficient, wherein the predictive coefficient has a numerical value that correlates to the presence of cardiac disease in the patient.

42. The method of claim 41, wherein said step of calculating a multifractal coefficient comprises the step of calculating a multifractal Holder coefficient.

43. The method of claim 40, wherein said step of applying a wavelet transform filter comprises the step of applying a MODWT wavelet transform filter.

44. The method of claim 40, further comprising the step of applying a wavelet transform filter to the data prior to the step of applying wavelet-based multifractal analysis.

45. The method of claim 40, further comprising the step of performing a cluster analysis to the data.

46. The method of claim 45, wherein said step of performing a cluster analysis comprises the step of performing a Levy flight cluster analysis.

47. The method of claim 40, further comprising the step of calculating a short-scale multifractal coefficient, wherein said short-scale multifractal coefficient characterizes the short-scale beat region of the data.

48. The method of claim 47, wherein said step of calculating a short-scale coefficient comprises the step of calculating a multifractal alpha coefficient.

49. The method of claim 48, wherein said multifractal alpha coefficient characterizes a scale of one of 1–8 and 1–16 beats.

50. The method of claim 40, further comprising the step of quantifying the multifractality of the data by generating a multifractal cascade coefficient.

51. The method of claim 50, wherein said step of quantifying the multifractality of the data includes the step of generating a quadratic coefficient, wherein the value of said quadratic coefficient is indicative of the degree of multifractality of the data.

52. The method of claim 51, wherein said quadratic coefficient is indicative of multifractal data when the quadratic coefficient has a value of about 11 or greater.

53. A method of evaluating a treatment regimen for heart disease, comprising the steps of:
(a) collecting electrocardiogram data;
(b) smoothing the data by applying a wavelet transform filter to the data; and
(c) applying wavelet-based multifractal analysis to the data.

54. The method of claim 53, wherein the step of applying multifractal analysis to the data comprises the step of calculating a multifractal predictive coefficient, wherein the predictive coefficient has a numerical value that correlates to the effectiveness of the treatment regimen.

55. The method of claim 54, wherein said step of calculating a multifractal coefficient comprises the step of calculating a multifractal Holder coefficient.

56. The method of claim 53, wherein said step of applying a wavelet transform filter comprises the step of applying a MODWT wavelet transform filter.

57. The method of claim 53, further comprising the step of performing a probability distribution on the data prior to the step of applying wavelet-based multifractal analysis.

58. The method of claim 53, further comprising the step of performing a cluster analysis to the data.

59. The method of claim 58, wherein said step of performing a cluster analysis comprises the step of performing a Levy flight cluster analysis.

60. The method of claim 53, further comprising the step of calculating a short-scale multifractal coefficient, wherein said short-scale multifractal coefficient characterizes the short-scale beat region of the data.

61. The method of claim 60, wherein said step of calculating a short-scale coefficient comprises the step of calculating a multifractal alpha coefficient.

62. The method of claim 61, wherein said multifractal alpha coefficient characterizes a scale of one of 1–8 and 1–16 beats.

63. The method of claim 53, further comprising the step of quantifying the multifractality of the data by generating a multifractal cascade coefficient.

64. The method of claim 63, wherein said step of quantifying the multifractality of the data includes the step of generating a quadratic coefficient, wherein the value of said quadratic coefficient is indicative of the degree of multifractality of the data.

65. The method of claim 64, wherein said quadratic coefficient is indicative of multifractal data when the quadratic coefficient has a value of about 11 or greater.

66. A method of evaluating a treatment regimen for heart disease, comprising the steps of:
(a) collecting electrocardiogram data;
(b) performing a probability distribution on the data; and
(c) applying wavelet-based multifractal analysis to the data.

67. The method of claim 66, wherein the step of applying multifractal analysis to the data comprises the step of calculating a multifractal predictive coefficient, wherein the predictive coefficient has a numerical value that correlates to the effectiveness of the treatment regimen.

68. The method of claim 67, wherein said step of calculating a multifractal coefficient comprises the step of calculating a multifractal Holder coefficient.

69. The method of claim 66, wherein said step of applying a wavelet transform filter comprises the step of applying a MODWT wavelet transform filter.

70. The method of claim 66, further comprising the step of applying a wavelet transform filter to the data prior to the step of applying wavelet-based multifractal analysis.

71. The method of claim 66, further comprising the step of performing a cluster analysis to the data.

72. The method of claim 71, wherein said step of performing a cluster analysis comprises the step of performing a Levy flight cluster analysis.

73. The method of claim 66, further comprising the step of calculating a short-scale multifractal coefficient, wherein said short-scale multifractal coefficient characterizes the short-scale beat region of the data.

74. The method of claim 73, wherein said step of calculating a short-scale coefficient comprises the step of calculating a multifractal alpha coefficient.

75. The method of claim 74, wherein said multifractal alpha coefficient characterizes a scale of one of 1–8 and 1–16 beats.

76. The method of claim 66, further comprising the step of quantifying the multifractality of the data by generating a multifractal cascade coefficient.

77. The method of claim 76, wherein said step of quantifying the multifractality of the data includes the step of generating a quadratic coefficient, wherein the value of said quadratic coefficient is indicative of the degree of multifractality of the data.

78. The method of claim 77, wherein said quadratic coefficient is indicative of multifractal data when the quadratic coefficient has a value greater than a threshold value.

79. A method for determining one of whether a patient has heart disease, a patient's risk of sudden death from a cardiac event, and the efficacy of a cardiac disease therapy, comprising the steps of:
(a) collecting EKG time series data for the patient;
(b) perform a cluster analysis on the data; and
(c) performing a multifractal alpha analysis on the data.

80. The method of claim 79, wherein said step of performing a cluster analysis comprises the step of performing a Levy flight analysis on the data.

81. The method of claim 80, wherein said step of performing a Levy flight analysis further comprises the step of determining a beat cluster index for the data.

82. The method of claim 79, wherein said step of performing a multifractal alpha analysis comprises the step of calculating an multifractal alpha coefficient for the data.

83. The method of claim 82, wherein said step of performing a multifractal alpha analysis further comprises the steps of calculating a critical multifractal alpha value and comparing the multifractal alpha coefficient to the critical multifractal alpha value.

84. The method of claim 79, further comprising the step of performing smoothing on the data.

85. The method of claim 84, wherein said smoothing step comprises the performance of wavelet smoothing on the data.

86. The method of claim 85, wherein said wavelet smoothing step comprises wavelet smoothing performed within a scaling range of 1–16 beats.

87. The method of claim 85, further comprising the step of calculating a multifractal cascade coefficient for the data.

88. The method of claim 87, further comprising the step of calculating a critical multifractal cascade value and comparing the multifractal cascade coefficient to the critical multifractal cascade value.

89. The method of claim 85, further comprising the step of performing multifractal Holder sequential smoothing on the data to generate a series of multifractal holder coefficients.

90. The method of claim 89, further comprising the step of determining if the multifractal holder coefficients increase over the course of the sequential smoothing step.

91. The method of claim 90, further comprising the step of calculating a critical multifractal Holder value and comparing the critical value to the multifractal holder coefficients.

92. The method of claim 84, wherein said smoothing step comprises the steps of generating a probability distribution function for the data wherein said probability distribution function has a head and a tail, and discarding at least some portion of the tail of the probability distribution function from the data.

93. The method of claim 84, wherein said smoothing step comprises the steps of generating wavelet ridges for the data and selectively removing at least some of the wavelet ridges that are related to intermittency in the data.

94. A method for determining one of whether a patient has heart disease, a patient's risk of sudden death from a cardiac event, and the efficacy of a cardiac disease therapy, comprising the steps of:

(a) collecting EKG time series data for the patient;

(b) performing a direct multifractal spectrum calculation from the EKG time series data; and (c) calculating one of a multifractal Holder analysis and a multifractal alpha analysis from the results of the step of performing a direct multifractal spectrum calculation.

95. A method for determining one of whether a patient has heart disease, a patient's risk of sudden death from a cardiac event, and the efficacy of a cardiac disease therapy, comprising the steps of:

(a) collecting EKG time series data for the patient; and (b) calculating one of Shannon entropy, Pesin metric and topological entropies, Kolmolgorov-Sinai entropy, approximate entropy, Lyapunov exponents, and a Tsallis entropic scaling coefficient from the EKG time series data.

96. The method of claim 94, wherein said step of calculating comprises the step of calculating a Tsallis entropic scaling coefficient according to the formula $1/H_{min} - 1/H_{max}$.

* * * * *